United States Patent
Mitchell et al.

(10) Patent No.: US 10,335,402 B2
(45) Date of Patent: Jul. 2, 2019

(54) SULFONYL PIPERIDINE DERIVATIVES AND THEIR USE FOR TREATING PROKINETICIN MEDIATED GASTROINTESTINAL DISORDERS

(71) Applicant: Takeda Pharmaceutical Company Limited, Osaka (JP)

(72) Inventors: Philip Mitchell, Cambridgeshire (GB); Martin Teall, Cambridgeshire (GB)

(73) Assignee: Takeda Pharmaceutical Company Limited (JP)

( * ) Notice: Subject to any disclaimer, the term of this patent is extended or adjusted under 35 U.S.C. 154(b) by 0 days.

(21) Appl. No.: 15/525,417

(22) PCT Filed: Nov. 11, 2015

(86) PCT No.: PCT/GB2015/053410
§ 371 (c)(1),
(2) Date: May 9, 2017

(87) PCT Pub. No.: WO2016/075457
PCT Pub. Date: May 19, 2016

(65) Prior Publication Data
US 2017/0340621 A1   Nov. 30, 2017

(30) Foreign Application Priority Data
Nov. 12, 2014 (GB) .................. 1420095.0

(51) Int. Cl.
*A61K 31/454* (2006.01)
*C07D 401/12* (2006.01)

(52) U.S. Cl.
CPC .......... *A61K 31/454* (2013.01); *C07D 401/12* (2013.01)

(58) Field of Classification Search
CPC .................................. A61K 31/454
See application file for complete search history.

(56) References Cited

U.S. PATENT DOCUMENTS

2013/0324576 A1   12/2013   Carroll et al.

FOREIGN PATENT DOCUMENTS

| EP | 1676844 | 7/2006 |
|---|---|---|
| WO | 2006034341 | 3/2006 |
| WO | 2006102112 A2 | 9/2006 |
| WO | 2007079214 | 7/2007 |
| WO | 2010077976 | 7/2010 |
| WO | 2010080864 | 7/2010 |
| WO | 2013179024 A1 | 5/2013 |
| WO | 2014202999 A1 | 12/2014 |

OTHER PUBLICATIONS

Watson et al. Neurogastroenterol. Motil., 2012, vol. 24, No. 1, Abstract.*
International Search Report, dated Dec. 1, 2016 for PCT Application No. PCT/GB2015/053410, filed Nov. 11, 2015.
International Preliminary Report on Patentability, dated May 26, 2017 for PCT Application No. PCT/GB2015/053410, filed Nov. 11, 2015.
GB Search Report, dated Aug. 11, 2015, in Application No. GB1420095.0.
Chemical Abstracts Registry No. 1436296-61-5; Entered STN: Jun. 9, 2013; 1-[(methyl-1H-pyrazol-4-yl)sulfonyl]-4-(phenylmethylene).
Chemical Abstracts Registry No. 1172299-59-0; Entered STN: Aug. 4, 2009; 1-[(1-cyclopentyl-3-(1,1-dimethyethyl)-1H-pyrazol-4-yl]sulfonyl]-4-(phenylmethyl).
Chemical Abstracts Registry No. 1171428-14-0; Entered STN: Aug. 2, 2009; 1-[(1-cyclopentyl-3-methyl-1H-pyrazol-4-yl]sulfonyl]-4-(phenylmethyl).
Chemical Abstracts Registry No. 1209259-27-7; Entered STN: Mar. 12, 2010; 1-[(5-chloro-1-methyl-1H-imidazol-4-y1)sulfonyl]-4-[(3-fluorphenyl)methylene].
Aziri et al., Phosphorus, Sulfur and Silicon, vol. 178(6), pp. 1255-1259, 2003.
Naresh et al. Bioorganic & Medicinal Chemistry, vol. 18(24), pp. 8679-8686, 2010.
Blackburn et al., Journal of the Chemical Society, Perkin Transactions 1, vol. 6, pp. 913-917, 1986.
International Search Report, dated Jan. 12, 2016 for PCT Application No. PCT/GB2015/053410, filed Nov. 11, 2015.

* cited by examiner

Primary Examiner — Samira J Jean-Louis
(74) Attorney, Agent, or Firm — Barnes & Thornburg LLP; Scott D. Rothenberger

(57) ABSTRACT

The present invention provides compounds of formula (I) and pharmaceutically acceptable salts thereof (Formula (I)) in which m, n, W, X, Y, Z, $R^1$, $R^2$, $R^3$, $R^4$ and $R^5$ are as defined in the specification for use in treating irritable bowel syndrome or inflammatory bowel disease.

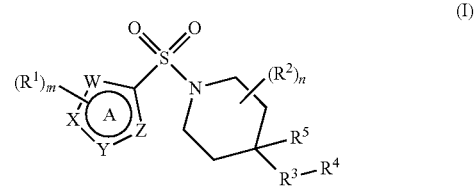

6 Claims, No Drawings

SULFONYL PIPERIDINE DERIVATIVES AND THEIR USE FOR TREATING PROKINETICIN MEDIATED GASTROINTESTINAL DISORDERS

CROSS-REFERENCE TO RELATED APPLICATIONS

This application is a Section 371 National Stage Application of International No. PCT/GB2015/053410, filed Nov. 11, 2015, and published as WO/2016/075457 A1 on May 19, 2016, which claims priority from GB Patent Application No. 1420095.0, filed Nov. 12, 2014, the contents of which are incorporated herein in their entirety for all purposes.

The present invention relates to the use of piperidine derivatives in therapy, particularly for the treatment or prevention of gastrointestinal-related conditions.

Prokineticins are cysteine-rich regulatory peptides that are thought to exert signaling activity via two highly conserved G protein-coupled receptors (GPCR), the prokineticin receptor 1 (PKR1 or PROKR1) and the prokineticin receptor 2 (PKR2 or PROKR2), that belong to the 7-transmembrane domain, G protein-coupled receptor (GPCR) superfamily.

Prokineticin receptor 1 (also known as GPR73) shows 87% homology to Prokineticin Receptor 2 (also known as GPR73L1). Prokineticins (PK1 and PK2) contain 86 and 81 amino acids respectively, sharing 45% amino acid identity. Both prokineticins activate the two prokineticin receptors, PKR1 and PKR2, with similar potency.

PKR1 receptors couple to $G_q/G_{11}$ proteins leading to phospholipase C activation, inositol phosphate production and calcium mobilization. In addition, activation of the mitogen-activated protein kinase (MAPK) pathways has also been described.

PKR1 is broadly distributed throughout peripheral tissues including the intestinal tract, testis, uterus, lung, mouse dorsal root ganglia, macrophage, bone, heart, rectum, white adipose and peripheral blood leukocytes. In addition, the receptor is expressed in the brain particularly in olfactory regions as well as in dorsal root ganglion (DRG) neurons, mouse hippocampus, dentate gyrus, cerebellar cortex, cerebral cortex, human hippocampus, amygdala, medulla oblongata and spinal cord.

Prokineticins were originally identified as potent agents mediating gut motility, but were later shown to promote angiogenesis in steroidogenic glands (e.g. adrenal gland), heart and reproductive systems. They also modulate neurogenesis, circadian rhythms, nociception, haematopoiesis as well as the immune response. Prokineticins are thought to be associated with pathologies of the reproductive and nervous systems, myocardial infarction and tumorigenesis.

Consequently, antagonisim of the functions of the prokineticins may have utility in the treatment of disorders or diseases including gastrointestinal motility, angiogenesis, hematopoiesis, diabetes (e.g. as described in International Patent Application Publication No. WO 2010/077976) and pain (e.g. as described in International Patent Application Publication No. WO 2007/079214).

Certain piperidine derivatives are known chemical library compounds with no known use that are available from commercial suppliers such as Ambinter and Ukrorgsyntez Ltd., in particular the following compounds having Chemical Abstracts Registry Nos. 1436296-61-5, 1172299-59-0, 1171428-14-0 and 1209259-27-7.

Certain other piperidine derivatives which are said to possess pharmacological properties are known, for example, from International Patent Application Publication Nos. WO 2006/034341 and WO 2010/080864.

In accordance with the present invention, there is therefore provided a compound of formula (I)

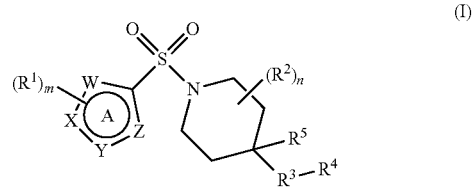

or a pharmaceutically acceptable salt thereof for use in treating irritable bowel syndrome or inflammatory bowel disease, wherein W, X, Y and Z each independently represent N, NH or CH, with the proviso that W, X, Y and Z do not each simultaneously represent a moiety CH;

m is 0, 1, 2 or 3;

each $R^1$ independently represents halogen, cyano, $C_1$-$C_6$ alkoxy, $C_3$-$C_6$ cycloalkyl, $C_1$-$C_6$ alkoxycarbonyl, $C_1$-$C_6$ haloalkyl, $C_1$-$C_6$ haloalkoxy, $C_1$-$C_6$ alkylthio, $C_1$-$C_6$ alkylcarbonyl, or $C_1$-$C_6$ alkyl optionally substituted by carboxyl or $C_1$-$C_6$ alkoxycarbonyl;

n is 0, 1, 2, 3 or 4;

each $R^2$ independently represents halogen, cyano, carboxyl, hydroxyl, $C_1$-$C_6$ alkyl, $C_1$-$C_6$ haloalkyl, $C_1$-$C_6$ alkoxy, $C_1$-$C_6$ hydroxyalkyl, $C_1$-$C_6$ alkoxycarbonyl, $C_1$-$C_6$ alkoxy$C_1$-$C_6$ alkyl or a 5- to 9-membered heterocyclic ring system;

$R^3$ represents $=CR^6$, or, when there is at least one $R^1$ group present that represents a $C_3$-$C_6$ cycloalkyl group, then $R^3$ may additionally represent a group —$CR^7R^8$—;

$R^5$ is absent or represents a hydrogen atom or a substituent as defined above for $R^2$;

$R^6$ represents a hydrogen or halogen atom or a cyano, $C_1$-$C_6$ alkyl or $C_1$-$C_6$ alkoxycarbonyl group;

$R^7$ and $R^8$ each independently represent a hydrogen or halogen atom or cyano, carboxyl, hydroxyl, $C_1$-$C_6$ alkyl, $C_1$-$C_6$ haloalkyl, $C_1$-$C_6$ alkoxy, $C_1$-$C_6$ hydroxyalkyl, $C_1$-$C_6$ alkoxycarbonyl, $C_1$-$C_6$ alkoxy$C_1$-$C_6$ alkyl or a 5- to 9-membered heterocyclic ring system;

$R^4$ represents a 6- to 10-membered aromatic or heteroaromatic ring system, the ring system itself being optionally substituted by at least one substituent selected from halogen, hydroxyl, cyano, oxo (=O), $C_1$-$C_6$ alkyl, $C_2$-$C_6$ alkenyl, $C_2$-$C_6$ alkynyl, $C_1$-$C_6$ haloalkyl, $C_1$-$C_6$ hydroxyalkyl, $C_1$-$C_6$ alkoxy, $C_1$-$C_6$ haloalkoxy, $C_1$-$C_6$ alkylthio, $C_1$-$C_6$ alkylsulphinyl, $C_1$-$C_6$ alkylsulphonyl, $C_1$-$C_6$ alkylcarbonyl, $C_1$-$C_6$ alkylcarbonyloxy, $C_1$-$C_6$ alkoxycarbonyl, amino (—$NH_2$), —$CON(R^9)_2$, $C_1$-$C_6$ alkylamino, di-($C_1$-$C_6$ alkyl)amino, $C_3$-$C_6$ cycloalkyl, $C_3$-$C_6$ cycloalkyloxy or $C_3$-$C_6$ cycloalkylmethyl; and each $R^9$ independently represents a hydrogen atom or a $C_1$-$C_6$ alkyl group.

The present invention also provides a compound of formula (I) or a pharmaceutically acceptable salt thereof as defined above for use in treating irritable bowel syndrome or inflammatory bowel disease, with the proviso that the compound of formula (I) is not:

1-[(1-methyl-1H-pyrazol-4-yl)sulfonyl]-4-(phenylmethylene)piperidine,

1-[[1-cyclopentyl-3-(1,1-dimethylethyl)-1H-pyrazol-4-yl]sulfonyl]-4-(phenylmethyl)piperidine, 1-[(1-cyclopentyl-3-methyl-1H-pyrazol-4-yl)sulfonyl-4-(phenylmethyl)piperidine, or 1-[(5-chloro-1-methyl-1H-imidazol-4-yl)sulfonyl]-4-[(3-fluorophenyl)-methylene]piperidine.

The present invention further provides the use of a compound of formula (I) or a pharmaceutically acceptable salt thereof as hereinbefore defined for the preparation of a medicament for the treatment of irritable bowel syndrome or inflammatory bowel disease.

In the context of the present specification, unless otherwise stated, an alkyl, alkenyl or alkynyl substituent group or an alkyl, alkenyl or alkynyl moiety in a substituent group may be linear or branched. Examples of $C_1$-$C_6$ alkyl groups/moieties include methyl, ethyl, propyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, tert-butyl, n-pentyl, isopentyl, neopentyl and n-hexyl. Examples of $C_2$-$C_6$ alkenyl groups/moieties include ethenyl, propenyl, 1-butenyl, 2-butenyl, 1-pentenyl, 1-hexenyl, 1,3-butadienyl, 1,3-pentadienyl, 1,4-pentadienyl and 1-hexadienyl. Examples of $C_2$-$C_6$ alkynyl groups/moieties include ethynyl, propynyl, 1-butynyl, 2-butynyl, 1-pentynyl and 1-hexynyl.

A $C_1$-$C_6$ haloalkyl or $C_1$-$C_6$ haloalkoxy substituent group/moiety will comprise at least one halogen atom, e.g. one, two, three, four or five halogen atoms, examples of which include trifluoromethyl, trifluoromethoxy or pentafluoroethyl.

A $C_1$-$C_6$ hydroxyalkyl substituent group/moiety will comprise at least one hydroxy group, e.g. one, two, three or four hydroxyl groups, examples of which include —$CH_2OH$, —$CH_2CH_2OH$, —$CH_2CH_2CH_2OH$, —$CH(OH)CH_2OH$, —$CH(CH_3)OH$ and —$CH(CH_2OH)_2$.

The alkyl groups in a di-$C_1$-$C_6$ alkylamino group/moiety may be the same as, or different from, one another.

The ring A in formula (I) is a 5-membered heteroaromatic ring containing from 1 to 4 ring nitrogen atoms, examples of which include pyrrolyl, imidazolyl, pyrazolyl, triazolyl and tetrazolyl.

A heterocyclic ring system means a saturated, partially unsaturated or fully unsaturated hydrocarbyl group containing from 5 to 9 ring atoms in which one or more (e.g. one, two, three or four) ring carbon atoms are replaced by a corresponding number of ring heteroatoms independently selected from nitrogen, oxygen and sulphur, particularly nitrogen and oxygen. Examples of heterocyclic ring systems include tetrahydrofuranyl, piperidinyl, pyrrolidinyl, tetrahydropyranyl, morpholinyl, thiamorpholinyl, dihydrobenzofuranyl, dihydrobenzothienyl and indolyl.

When any chemical moiety or group in formula (I) is described as being optionally substituted, it will be appreciated that the moiety or group may be either unsubstituted or substituted by one or more of the specified substituents. It will be appreciated that the number and nature of substituents will be selected so as to avoid sterically undesirable combinations.

In ring A of the compounds of formula (I), at least one of W, X, Y and Z represents N or NH. In one aspect of the invention, Y represents N or NH and W, X and Z each independently represent N, NH or CH. In a further aspect, Y represents N and W, X and Z each represent CH.

In one embodiment of the invention, at least two of W, X, Y and Z represent N or NH. Particularly advantageous compounds are those in which (i) X and Y each independently represent N or NH and W and Z both represent CH, or (ii) Y and Z each independently represent N or NH and W and X both represent CH, or (iii) W and X each independently represent N or NH and Y and Z both represent CH.

In another embodiment, at least three of W, X, Y and Z independently represent N or NH.

Specific examples of ring A, in which m and $R^1$ are as previously defined, include:

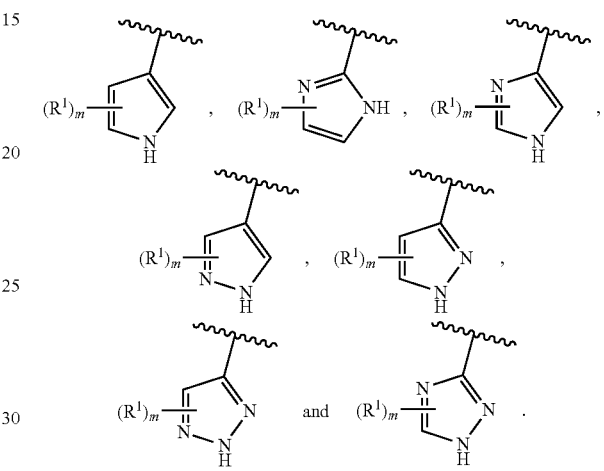

Advantageously, the ring A (where the substituents $R^1$, which may be the same or different, are as previously defined) is selected from the following moieties:

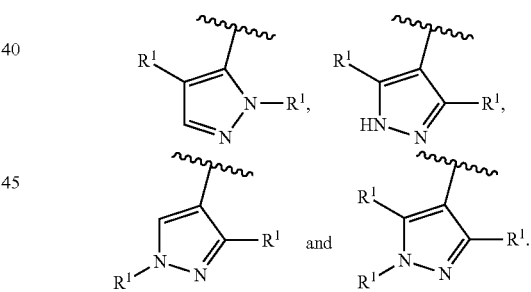

In particular, the ring A may be selected from one of the following moieties:

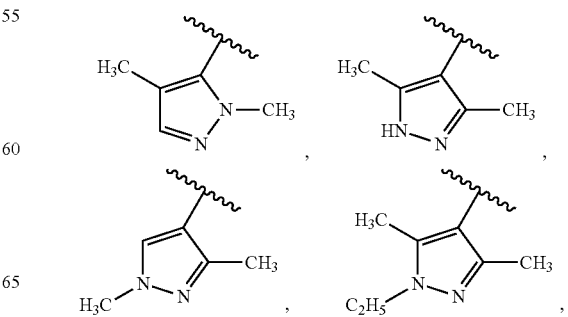

-continued

 ,  ,

 ,  ,

 ,  ,

 and  .

The number (m) of substituents $R^1$ on ring A may be 0, 1, 2 or 3, preferably 2 or 3.

If present on ring A, each $R^1$ independently represents halogen (e.g. fluorine, chlorine or bromine), cyano, $C_1$-$C_6$, or $C_1$-$C_4$, or $C_1$-$C_2$ alkoxy, $C_3$-$C_6$ or $C_3$-$C_5$ cycloalkyl, $C_1$-$C_6$, or $C_1$-$C_4$, or $C_1$-$C_2$ alkoxycarbonyl, $C_1$-$C_6$, or $C_1$-$C_4$, or $C_1$-$C_2$ haloalkyl, $C_1$-$C_6$, or $C_1$-$C_4$, or $C_1$-$C_2$ haloalkoxy, $C_1$-$C_6$, or $C_1$-$C_4$, or $C_1$-$C_2$ alkylthio, $C_1$-$C_6$, or $C_1$-$C_4$, or $C_1$-$C_2$ alkylcarbonyl, or $C_1$-$C_6$, or $C_1$-$C_4$, or $C_1$-$C_2$ alkyl optionally substituted by one or more (e.g. one, two, three or four) substituents independently selected from carboxyl and $C_1$-$C_6$, or $C_1$-$C_4$, or $C_1$-$C_2$ alkoxycarbonyl.

In an embodiment of the invention, each $R^1$ independently represents halogen (e.g. fluorine, chlorine or bromine), cyano, $C_1$-$C_2$ alkoxy, $C_3$-$C_5$ cycloalkyl (e.g. cyclopropyl), $C_1$-$C_2$ alkoxycarbonyl, $C_1$-$C_2$ haloalkyl (e.g. difluoromethyl or trifluoromethyl), $C_1$-$C_2$ haloalkoxy (e.g. difluoromethoxy or trifluoromethoxy), $C_1$-$C_2$ alkylthio, $C_1$-$C_2$ alkylcarbonyl, or $C_1$-$C_6$, or $C_1$-$C_4$, or $C_1$-$C_2$ alkyl optionally substituted by one or more (e.g. one, two, three or four) substituents independently selected from carboxyl and $C_1$-$C_6$, or $C_1$-$C_4$, or $C_1$-$C_2$ alkoxycarbonyl.

In another embodiment, each $R^1$ independently represents halogen (e.g. fluorine, chlorine or bromine, especially chlorine), $C_3$-$C_5$ cycloalkyl (e.g. cyclopropyl), $C_1$-$C_2$ haloalkyl (e.g. difluoromethyl or trifluoromethyl) or $C_1$-$C_6$, or $C_1$-$C_4$, or $C_1$-$C_2$ alkyl (especially methyl or ethyl).

In still another embodiment, each $R^1$ independently represents cyclopropyl, $C_1$-$C_2$ haloalkyl (e.g. difluoromethyl or trifluoromethyl) or $C_1$-$C_2$ alkyl.

The number (n) of substituents $R^2$ on the piperidine ring may be 0, 1, 2, 3 or 4, and is preferably 0 or 1. A substituent $R^2$ may be attached at any suitable position on the piperidine ring but is preferably attached at the 3-position (or meta position) relative to the ring nitrogen atom.

If present, each $R^2$ independently represents halogen (e.g. fluorine, chlorine or bromine), cyano, carboxyl, hydroxyl, $C_1$-$C_6$, or $C_1$-$C_4$, or $C_1$-$C_2$ alkyl, $C_1$-$C_6$, or $C_1$-$C_4$, or $C_1$-$C_2$ haloalkyl, $C_1$-$C_6$, or $C_1$-$C_4$, or $C_1$-$C_2$ alkoxy, $C_1$-$C_6$, or $C_1$-$C_4$, or $C_1$-$C_2$ hydroxyalkyl, $C_1$-$C_6$, or $C_1$-$C_4$, or $C_1$-$C_2$ alkoxycarbonyl, $C_1$-$C_6$, or $C_1$-$C_4$, or $C_1$-$C_2$ alkoxy$C_1$-$C_6$ alkyl or a 5-, 6-, 7-, 8- or 9-membered heterocyclic ring system.

In one embodiment, each $R^2$ independently represents halogen (e.g. fluorine, chlorine or bromine), cyano, carboxyl, hydroxyl, $C_1$-$C_2$ alkyl (especially methyl), $C_1$-$C_2$ haloalkyl (e.g. difluoromethyl or trifluoromethyl), $C_1$-$C_2$ alkoxy (especially methoxy), $C_1$-$C_2$ hydroxyalkyl (e.g. hydroxymethyl), $C_1$-$C_2$ alkoxycarbonyl (especially ethoxycarbonyl), $C_1$-$C_2$ alkoxy$C_1$-$C_6$ alkyl (preferably $C_1$-$C_2$ alkoxy$C_1$-$C_2$ alkyl) or a 5- to 6-membered heterocyclic ring system containing one or two ring heteroatoms independently selected from nitrogen and oxygen.

In another embodiment, each $R^2$ independently represents halogen (especially fluorine), cyano, hydroxyl, $C_1$-$C_2$ alkyl (especially methyl), $C_1$-$C_2$ alkoxy (especially methoxy), $C_1$-$C_2$ alkoxycarbonyl (especially ethoxycarbonyl), or $C_1$-$C_2$ alkoxy$C_1$-$C_2$ alkyl (particularly methoxymethyl).

In still another embodiment, each $R^2$ independently represents cyano, hydroxyl, $C_1$-$C_2$ alkyl (especially methyl), $C_1$-$C_2$ alkoxy (especially methoxy), $C_1$-$C_2$ alkoxycarbonyl (especially ethoxycarbonyl), or $C_1$-$C_2$ alkoxy$C_1$-$C_2$ alkyl (particularly methoxymethyl).

In a further embodiment, n is 1 and $R^2$ is methyl.

$R^3$ represents $=CR^6$, or, when there is at least one $R^1$ group present that represents a $C_3$-$C_6$ cycloalkyl group, then $R^3$ may additionally represent a group $-CR^7R^8-$.

In one embodiment of the invention, $R^3$ may represent $=CR^6$ where $R^6$ represents a hydrogen or halogen (e.g. fluorine, chlorine or bromine) atom or a cyano, $C_1$-$C_6$, or $C_1$-$C_4$, or $C_1$-$C_2$ alkyl or $C_1$-$C_6$, or $C_1$-$C_4$, or $C_1$-$C_2$ alkoxycarbonyl group.

In another embodiment, $R^6$ represents a hydrogen or fluorine atom or a cyano, $C_1$-$C_2$ alkyl (particularly methyl) or $C_1$-$C_2$ alkoxycarbonyl (particularly methoxycarbonyl) group.

In a preferred aspect, $R^6$ represents a fluorine atom.

In a further embodiment of the invention, $R^3$ may represent a group $-CR^7R^8-$ where $R^7$ and $R^8$ each independently represent a hydrogen or halogen (e.g. fluorine, chlorine or bromine) atom, cyano, carboxyl, hydroxyl, $C_1$-$C_6$, or $C_1$-$C_4$, or $C_1$-$C_2$ alkyl, $C_1$-$C_6$, or $C_1$-$C_4$, or $C_1$-$C_2$ haloalkyl, $C_1$-$C_6$, or $C_1$-$C_4$, or $C_1$-$C_2$ alkoxy, $C_1$-$C_6$, or $C_1$-$C_4$, or $C_1$-$C_2$ hydroxyalkyl, $C_1$-$C_6$, or $C_1$-$C_4$, or $C_1$-$C_2$ alkoxycarbonyl, $C_1$-$C_6$, or $C_1$-$C_4$, or $C_1$-$C_2$ alkoxy$C_1$-$C_6$ alkyl or a 5-, 6-, 7-, 8- or 9-membered heterocyclic ring system.

In one aspect, $R^7$ and $R^8$ each independently represent a hydrogen or halogen (e.g. fluorine, chlorine or bromine) atom, cyano, hydroxyl, $C_1$-$C_2$ alkyl (preferably methyl), $C_1$-$C_2$ haloalkyl (e.g. difluoromethyl or trifluoromethyl), $C_1$-$C_2$ alkoxy, $C_1$-$C_2$ hydroxyalkyl (e.g. hydroxymethyl), or $C_1$-$C_2$ alkoxy$C_1$-$C_2$ alkyl (particularly methoxymethyl). In a preferred aspect, $R^7$ and $R^8$ each represent a hydrogen atom.

In particular, $R^3$ may represent $CH_2$, $=CH$, $=CF$, $=C(CN)$, $=C(CH_3)$ or $=C(CO_2CH_3)$. Advantageously, $R^3$ represents $=CF$.

$R^5$ is absent (i.e. when $R^3$ represents $=CR^6$) or represents a hydrogen atom or a substituent as defined above for $R^2$.

In one aspect, $R^5$ represents a hydrogen atom.

In another aspect, $R^5$ is absent.

$R^4$ represents a 6-, 7-, 8-, 9- or 10-membered aromatic or heteroaromatic ring system, the ring system itself being optionally substituted by at least one substituent (e.g. one, two, three or four substituents independently) selected from halogen (e.g. fluorine, chlorine or bromine), hydroxyl, cyano, oxo ($=O$), $C_1$-$C_6$, or $C_1$-$C_4$, or $C_1$-$C_2$ alkyl, $C_2$-$C_6$ or $C_2$-$C_4$ alkenyl, $C_2$-$C_6$ or $C_2$-$C_4$ alkynyl, $C_1$-$C_6$, or $C_1$-$C_4$, or $C_1$-$C_2$ haloalkyl, $C_1$-$C_6$, or $C_1$-$C_4$, or $C_1$-$C_2$ hydroxyalkyl, $C_1$-$C_6$, or $C_1$-$C_4$, or $C_1$-$C_2$ alkoxy, $C_1$-$C_6$, or $C_1$-$C_4$, or $C_1$-$C_2$ haloalkoxy, $C_1$-$C_6$, or $C_1$-$C_4$, or $C_1$-$C_2$ alkylthio, $C_1$-$C_6$, or $C_1$-$C_4$, or $C_1$-$C_2$ alkylsulphinyl, $C_1$-$C_6$, or $C_1$-$C_4$, or $C_1$-$C_2$ alkylsulphonyl, $C_1$-$C_6$, or $C_1$-$C_4$, or $C_1$-$C_2$ alkylcarbonyl, $C_1$-$C_6$, or $C_1$-$C_4$, or $C_1$-$C_2$ alkylcarbonyloxy, $C_1$-$C_6$, or $C_1$-$C_4$, or $C_1$-$C_2$ alkoxycarbonyl, amino (—$NH_2$), —CON($R^9$)$_2$, $C_1$-$C_6$, or $C_1$-$C_4$, or $C_1$-$C_2$ alkylamino, di-($C_1$-$C_6$ alkyl)amino, $C_3$-$C_6$ cycloalkyl, $C_3$-$C_6$ cycloalkyloxy and $C_3$-$C_6$ cycloalkylmethyl.

The heteroaromatic ring system will comprise at least one ring heteroatom (e.g. one, two, three or four ring heteroatoms independently) selected from nitrogen, sulphur and oxygen. Preferably the ring heteroatoms are selected from nitrogen and oxygen.

Examples of 6- to 10-membered aromatic or heteroaromatic ring systems that may be used, which may be monocyclic or polycyclic (e.g. bicyclic) in which the two or more rings are fused, include one or more (in any combination) of phenyl, pyridinyl, naphthyl, benzofuranyl, benzothienyl, quinolinyl, imidazo[1,2-a]pyridinyl, pyrazinyl, indolyl, pyrimidinyl, thiophenyl and benzimidazolyl. Preferred ring systems include phenyl, quinolinyl, naphthyl and pyridinyl.

In one embodiment of the invention, $R^4$ represents a 6-, 7-, 8-, 9- or 10-membered aromatic or heteroaromatic ring system, the ring system itself being optionally substituted by at least one substituent (e.g. one, two, three or four substituents independently) selected from halogen (e.g. fluorine, chlorine or bromine), hydroxyl, cyano, oxo, $C_1$-$C_4$ alkyl (e.g. methyl or ethyl), $C_2$-$C_4$ alkenyl (e.g. ethenyl), $C_2$-$C_4$ alkynyl (e.g. ethynyl), $C_1$-$C_2$ haloalkyl (e.g. trifluoromethyl), $C_1$-$C_2$ hydroxyalkyl (e.g. hydroxymethyl), $C_1$-$C_4$ alkoxy (e.g. methoxy or ethoxy), $C_1$-$C_2$ haloalkoxy (e.g. trifluoromethoxy), $C_1$-$C_4$ alkylthio (e.g. methylthio or ethylthio), $C_1$-$C_4$ alkylsulphinyl (e.g. methylsulphinyl or ethylsulphinyl), $C_1$-$C_4$ alkylsulphonyl (e.g. methylsulphonyl or ethylsulphonyl), $C_1$-$C_4$ alkylcarbonyl (e.g. methylcarbonyl or ethylcarbonyl), $C_1$-$C_4$ alkylcarbonyloxy (e.g. methylcarbonyloxy), $C_1$-$C_4$ alkoxycarbonyl (e.g. methoxycarbonyl), amino, —CON($R^9$)$_2$, $C_1$-$C_4$ alkylamino (e.g. methylamino or ethylamino), di-($C_1$-$C_4$ alkyl)amino (e.g. dimethylamino), $C_3$-$C_5$ cycloalkyl, $C_3$-$C_5$ cycloalkyloxy and $C_3$-$C_5$ cycloalkylmethyl.

In another embodiment of the invention, $R^4$ represents a 6-, 7-, 8-, 9- or 10-membered, particularly 6-membered, aromatic or heteroaromatic ring system (particularly a nitrogen-containing heteroaromatic ring system containing 1, 2, 3 or 4 ring nitrogen atoms and optionally one or more further ring heteroatoms), the ring system itself being optionally substituted by at least one substituent (e.g. one, two, three or four substituents independently) selected from halogen (e.g. fluorine, chlorine or bromine), cyano, $C_1$-$C_4$ alkyl (e.g. methyl or ethyl), $C_1$-$C_2$ haloalkyl (e.g. trifluoromethyl), $C_1$-$C_4$ alkoxy (e.g. methoxy or ethoxy) and $C_1$-$C_2$ haloalkoxy (e.g. trifluoromethoxy).

In still another embodiment of the invention, $R^4$ represents a 6-, 7-, 8-, 9- or 10-membered, particularly 6-membered, aromatic or heteroaromatic (particularly a nitrogen-containing heteroaromatic) ring system, the ring system itself being optionally substituted by at least one substituent (preferably up to three, most preferably one or two, substituents independently) selected from halogen (e.g. fluorine, chlorine or bromine), cyano, methyl, trifluoromethyl, methoxy and trifluoromethoxy.

In a still further embodiment of the invention, $R^4$ represents phenyl optionally substituted by at least one substituent (preferably up to three, most preferably one or two, substituents independently) selected from halogen (particularly fluorine or chlorine) and trifluoromethoxy.

Each $R^9$ independently represents a hydrogen atom or a $C_1$-$C_6$, or $C_1$-$C_4$, or $C_1$-$C_2$ alkyl, particularly methyl, group.

In a preferred embodiment of the invention, subject to the above provisos, compounds of formula (I) are those in which:

W, X, Y and Z each independently represent a nitrogen atom or a moiety NH or CH, with the proviso that W, X, Y and Z do not each simultaneously represent a moiety CH;

m is 2 or 3;

each $R^1$ independently represents $C_3$-$C_6$ cycloalkyl, $C_1$-$C_6$ haloalkyl or $C_1$-$C_6$ alkyl;

n is 0 or 1;

$R^2$ represents $C_1$-$C_6$ alkyl;

$R^3$ represents =$CR^6$, or, when there is at least one $R^1$ group present that represents a $C_3$-$C_6$ cycloalkyl group, then $R^3$ may additionally represent a group —$CR^7R^8$—;

$R^5$ is absent or represents a hydrogen atom;

$R^6$ represents a hydrogen or fluorine atom or a cyano, $C_1$-$C_2$ alkyl or $C_1$-$C_2$ alkoxycarbonyl group;

$R^7$ and $R^8$ each represent a hydrogen atom; and $R^4$ represents a 6- to 10-membered aromatic or heteroaromatic ring system, the ring system itself being optionally substituted by at least one substituent selected from halogen and $C_1$-$C_6$ haloalkoxy.

Examples of compounds of formula (I) for use in the invention include:

4-(4-Chloro-3-fluorobenzyl)-1-((3-cyclopropyl-5-methyl-1H-pyrazol-4-yl)sulfonyl)piperidine, Methyl 2-(4-Chlorophenyl)-2-(1-((3,5-dimethyl-1H-pyrazol-4-yl)sulfonyl)piperidin-4-ylidene)acetate, 2-(4-Chlorophenyl)-2-(1-((3,5-dimethyl-1H-pyrazol-4-yl)sulfonyl)piperidin-4-ylidene)acetonitrile, 2-(2,6-Difluorophenyl)-2-(1-((3,5-dimethyl-1H-pyrazol-4-yl)sulfonyl)piperidin-4-ylidene)acetonitrile, 2-(4-Chloro-2-fluorophenyl)-2-(1-((3,5-dimethyl-1H-pyrazol-4-yl)sulfonyl)piperidin-4-ylidene)acetonitrile, 2-(4-Chlorophenyl)-2-(1-((3,5-diethyl-1H-pyrazol-4-yl)sulfonyl)piperidin-4-ylidene)acetonitrile, 2-(4-Chlorophenyl)-2-(1-((1,5-dimethyl-3-(trifluoromethyl)-1H-pyrazol-4-yl)sulfonyl)piperidin-4-ylidene)acetonitrile, 2-(2,6-Difluorophenyl)-2-(1-((1,3,5-trimethyl-1H-pyrazol-4-yl)sulfonyl)piperidin-4-ylidene)acetonitrile, 2-(1-((3,5-Dimethyl-1H-pyrazol-4-yl)sulfonyl)piperidin-4-ylidene)-2-(4-(trifluoromethoxy)phenyl)acetonitrile, 2-(4-Chlorophenyl)-2-(1-((3,5-dimethyl-1H-pyrazol-4-yl)sulfonyl)-3-methylpiperidin-4-ylidene)acetonitrile, 4-(4-Chloro-2-fluorobenzylidene)-1-((3,5-dimethyl-1H-pyrazol-4-yl)sulfonyl)piperidine, 4-(4-Chloro-2-fluorobenzylidene)-1-((1,3,5-trimethyl-1H-pyrazol-4-yl)sulfonyl)piperidine, 4-(1-(4-Chlorophenyl)ethylidene)-1-((3,5-dimethyl-1H-pyrazol-4-yl)sulfonyl)piperidine, 4-(4-Chlorobenzylidene)-1-((3,5-dimethyl-1H-pyrazol-4-yl)sulfonyl)piperidine, 2-(4-Chlorophenyl)-2-(1-((1,3,5-trimethyl-1H-pyrazol-4-yl)sulfonyl)piperidin-4-ylidene)acetonitrile, 4-((4-Chlorophenyl)fluoromethylene)-1-((3,5-dimethyl-1H-pyrazol-4-yl)sulfonyl)piperidine, 4-((3-Chloro-4-fluorophenyl)fluoromethylene)-1-((3,5-dimethyl-1H-pyrazol-4-yl)sulfonyl)piperidine, 4-((2,4-Dichlorophenyl)fluoromethylene)-1-((3,5-dimethyl-1H-pyrazol-4-yl)sulfonyl)piperidine, 4-((3,4-Dichlorophenyl)fluoromethylene)-1-((3,5-dimethyl-1H-pyrazol-4-yl)sulfonyl)piperidine,
4-((4-Chloro-3-fluorophenyl)fluoromethylene)-1-((3,5-dimethyl-1H-pyrazol-4-yl)sulfonyl)piperidine,
4-((4-Chloro-2-fluorophenyl)fluoromethylene)-1-((3,5-dimethyl-1H-pyrazol-4-yl)sulfonyl)piperidine,
4-((2,4-Difluorophenyl)fluoromethylene)-1-((3,5-dimethyl-1H-pyrazol-4-yl)sulfonyl)piperidine,
3-((1-((3,5-Dimethyl-1H-pyrazol-4-yl)sulfonyl)piperidin-4-ylidene)fluoromethyl)quinoline,
and pharmaceutically acceptable salts of any one thereof.

Compounds of formula (I) and pharmaceutically acceptable salts thereof as defined above may be prepared by a process comprising reacting a compound of formula

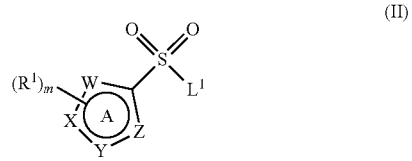

(II)

wherein $L^1$ represents a leaving group (e.g. a halogen atom) and m, W, X, Y, Z and $R^1$ are as defined in formula (I), with a compound of formula

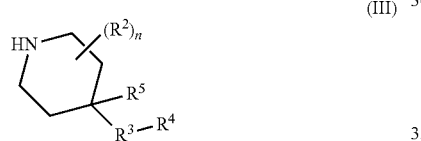

(III)

or a suitable salt (e.g. a hydrochloride salt) thereof, wherein n, $R^2$, $R^3$, $R^4$ and $R^5$ are as defined in formula (I);
and optionally thereafter carrying out one or more of the following procedures:
converting a compound of formula (I) into another compound of formula (I)
removing any protecting groups
forming a pharmaceutically acceptable salt.

The process may conveniently be carried out in the presence of an organic solvent such as dichloromethane, acetonitrile or tetrahydrofuran and a suitable base such as triethylamine, pyridine or diisopropylethylamine, at a temperature in the range from 20° C. to 40° C., e.g. at ambient temperature (20° C.).

Compounds of formula (II) in which $L^1$ represents a halogen atom may be prepared by reacting a compound of formula

(IV)

wherein m, W, X, Y, Z and $R^1$ are as defined in formula (I), with sulphur dioxide in the present of an organometallic reagent (e.g. an organolithium reagent such as n-butyl lithium), followed by reaction with a halogenating agent, e.g. N-chlorosuccinimide.

The first step of the process is conveniently carried out in the presence of an organic polar solvent such as ether, chloroform or dichloromethane under a nitrogen atmosphere at low temperature, e.g. from 0° C. to −70° C. The second step of the process may be carried out using a biphasic solvent mixture, e.g. dichloromethane/water mixture, at ambient temperature (20° C.).

Compounds of formula (III) in which $R^3$ represents =$CR^6$, $R^6$ represents cyano or $C_1$-$C_6$ alkoxycarbonyl and $R^5$ is absent may be prepared by reacting a compound of formula

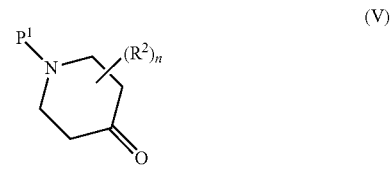

(V)

wherein $P^1$ represents a nitrogen-protecting group (e.g. tert-butoxy carbonyl group) and n and R are as defined in formula (I), with a compound of formula (VI), $R^{6'}$—$CH_2$—$R^4$ wherein $R^{6'}$ represents cyano or $C_1$-$C_6$ alkoxycarbonyl and $R^4$ is as defined in formula (I), in the presence of a strong base (e.g. sodium hydride), followed by an activation and elimination step (e.g. in the presence of thionyl chloride) and removal of the protecting group $P^1$ (e.g. in the presence of an acid such as hydrochloric acid) (see Scheme 1 below).

Scheme 1

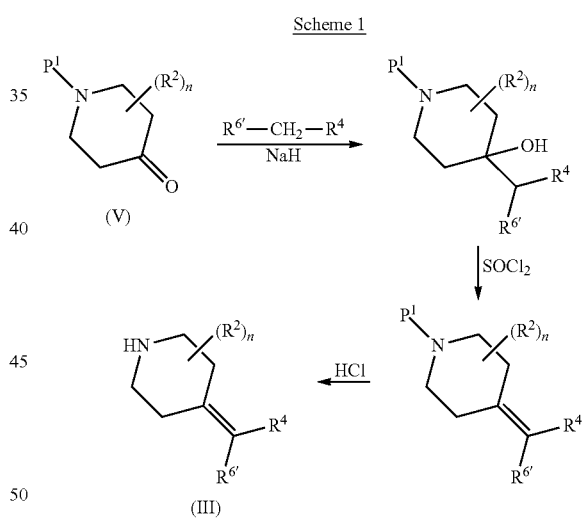

Alternatively, compounds of formula (III) in which $R^3$ represents =$CR^6$, $R^6$ represents a halogen atom and $R^5$ is absent may be prepared by a modified Arbamov reaction as illustrated in Scheme 2 below. Details of the Arbamov reaction can be found, for example, in the following literature references:
(1) Azizi, Najmedin and Saidi, Mohammad R., *Phosphorus, Sulfur and Silicon and the Related Elements*, 178(6), 1255-1259; 2003;
(2) Naresh S. Tulsi, A. Michael Downey, Christopher W. Cairo, *Bioorganic & Medicinal Chemistry*, 18 (2010), 8679-8686; and
(3) Blackburn, G. Michael and Kent, David E., *Journal of the Chemical Society, Perkin Transactions 1: Organic and Bio-Organic Chemistry* (1972-1999), (6), 913-17; 1986.

Scheme 2

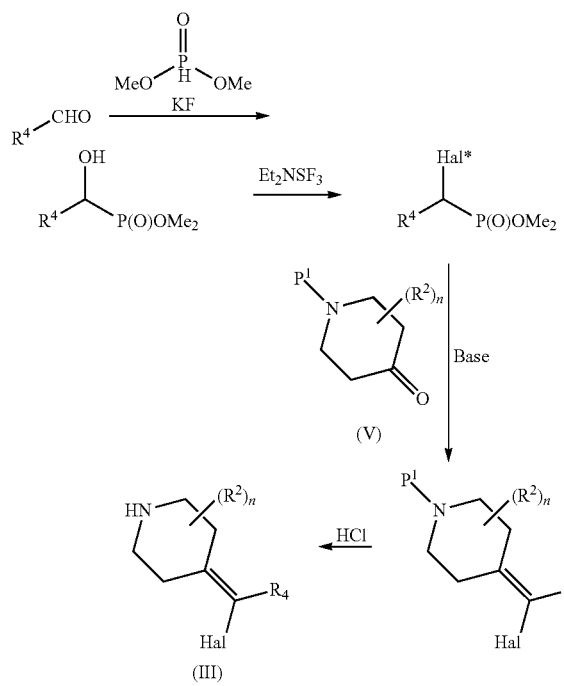

*Hal denotes halogen

Compounds of formula (III) in which $R^3$ represents =$CR^6$, $R^6$ represents a hydrogen atom or a $C_1$-$C_6$ alkyl group and $R^5$ is absent may be prepared via generation of a phosphonium salt as illustrated in Scheme 3 following:

Scheme 3

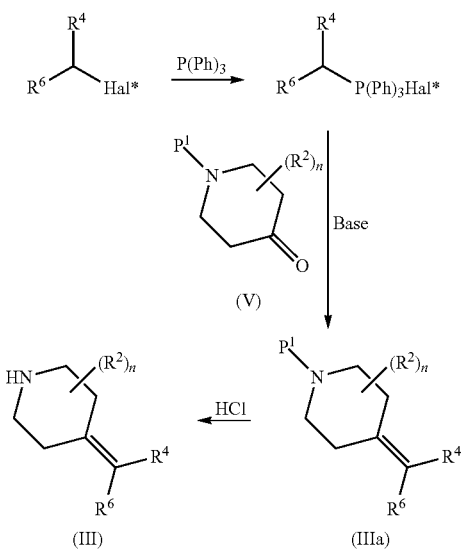

*Hal denotes halogen atom

The base used in Scheme 3 is preferably a strong base such as n-butyl lithium.

Compounds of formula (IIIa) in which $R^6$ represents a $C_1$-$C_6$ alkyl group may be synthesised according to Scheme 4 below:

Scheme 4

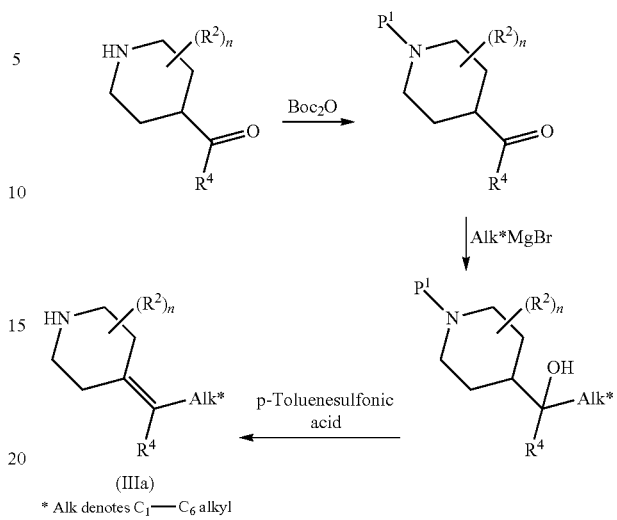

* Alk denotes $C_1$—$C_6$ alkyl

Compounds of formula (III) in which $R^3$ represents a group —$CR^7R^8$— and $R^7$ and $R^8$ each represent a hydrogen atom may be prepared by reducing a compound of formula (IIIa) in which $R^6$ represents a hydrogen atom, in a suitable solvent (e.g. an alcoholic solvent or ethyl acetate) in the presence of a metal catalyst (e.g. platinum (IV) oxide) under a hydrogen atmosphere, followed by removal of the protecting group, $P^1$, under acid conditions.

Compounds of formulae (III), (IV), (V) and (VI) are either commercially available, are well known in the literature or may be prepared using known techniques.

It will be appreciated by those skilled in the art that in the above processes certain functional groups such as phenol, hydroxyl or amino groups in the reagents may need to be protected by protecting groups. Thus, the preparation of compounds of formula (I) may involve, at an appropriate stage, the removal of one or more protecting groups.

The protection and deprotection of functional groups is described in 'Protective Groups in Organic Chemistry', edited by J. W. F. McOmie, Plenum Press (1973) and 'Protective Groups in Organic Synthesis', $3^{rd}$ edition, T. W. Greene and P. G. M. Wuts, Wiley-Interscience (1999).

The compounds of formula (I) above may be converted to a pharmaceutically acceptable salt thereof, preferably an acid addition salt such as a formate, hemi-formate, hydrochloride, hydrobromide, benzenesulphonate (besylate), saccharin (e.g. monosaccharin), trifluoroacetate, sulphate, nitrate, phosphate, acetate, fumarate, maleate, tartrate, lactate, citrate, pyruvate, succinate, valerate, propanoate, butanoate, malonate, oxalate, 1-hydroxy-2-napthoate (xinafoate), methanesulphonate or p-toluenesulphonate salt.

Compounds of formula (I) defined above may bear one or more radiolabels. Such radiolabels may be introduced by using radiolabel-containing reagents in the synthesis of the compounds of formula (I) or may be introduced by coupling the compounds of formula (I) to chelating moieties capable of binding to a radioactive metal atom. Such radiolabeled versions of the compounds may be used, for example, in diagnostic imaging studies.

Compounds of formula (I) and their salts may be in the form of hydrates or solvates. Such solvates may be formed with common organic solvents, including but not limited to, alcoholic solvents e.g. methanol, ethanol or isopropanol.

Compounds of formula (I) above may be capable of existing in stereoisomeric forms. It will be understood that the invention encompasses the use of all geometric and optical isomers (including atropisomers) of the compounds of formula (I) and mixtures thereof including racemates. The use of tautomers and mixtures thereof also form an aspect of the present invention.

The compounds of formula (I) and their pharmaceutically acceptable salts have activity as pharmaceuticals, in particular as prokineticin receptor modulators, and thus may be used in the treatment of gastrointestinal disorders (e.g. irritable bowel syndrome (IBS) and functional dyspepsia); and inflammatory conditions selected from the group consisting of inflammatory bowel disease (e.g. Crohn's disease, Coeliac disease, ileitis, ulcerative colitis, enteropathy associated with seronegative arthropathies, microscopic or collagenous colitis, eosinophilic gastroenteritis, or pouchitis resulting after proctocolectormy and ileoanal anastomosis), cholecystitis, cholangitis, Behcet's disease, pericholangitis, graft versus host disease, sarcoidosis, chronic gastritis (e.g. autoimmune gastritis) and rheumatoid arthritis. The compounds of formula (I) may also be used to treat addiction (e.g. drug addiction, alcohol addiction and nicotine addiction).

In the context of the present specification, the term "therapy" also includes "prophylaxis" unless there are specific indications to the contrary. The terms "therapeutic" and "therapeutically" should be construed accordingly.

Prophylaxis is expected to be particularly relevant to the treatment of persons who have suffered a previous episode of, or are otherwise considered to be at increased risk of, the disorder or condition in question. Persons at risk of developing a particular disorder or condition generally include those having a family history of the disorder or condition, or those who have been identified by genetic testing or screening to be particularly susceptible to developing the disorder or condition or those in the prodromal phase of a disorder.

In particular, the compounds of formula (I) and their pharmaceutically acceptable salts as defined above may be used in the treatment of the positive symptoms of schizophrenia, schizophreniform disorder or schizoaffective disorder (e.g. voices or hallucinations), cognitive disorders (such as dementia and impaired learning) and also pain (such as neuropathic pain).

The invention also provides a method of treating gastrointestinal disorders (e.g. irritable bowel syndrome (IBS) and functional dyspepsia); inflammatory conditions selected from the group consisting of inflammatory bowel disease (e.g. Crohn's disease, Coeliac disease, ileitis, ulcerative colitis, enteropathy associated with seronegative arthropathies, microscopic or collagenous colitis, eosinophilic gastroenteritis, or pouchitis resulting after proctocolectomy and ileoanal anastomosis), cholecystitis, cholangitis, Behcet's disease, pericholangitis, graft versus host disease, sarcoidosis, chronic gastritis (e.g. autoimmune gastritis) and rheumatoid arthritis; or addiction (e.g. drug addiction, alcohol addiction and nicotine addiction) which comprises administering to a patient in need thereof a therapeutically effective amount of a compound of formula (I) or a pharmaceutically acceptable salt thereof as hereinbefore defined.

For the above-mentioned therapeutic uses the dosage administered will, of course, vary with the compound employed, the mode of administration, the treatment desired and the disorder indicated. For example, the daily dosage of a compound in accordance with the invention (i.e. a compound of formula (I) or a pharmaceutically acceptable salt thereof), if inhaled, may be in the range from 0.05 micrograms per kilogram body weight (μg/kg) to 100 micrograms per kilogram body weight (μg/kg). Alternatively, if the compound is administered orally, then the daily dosage of the compound of the invention may be in the range from 0.01 micrograms per kilogram body weight (μg/kg) to 100 milligrams per kilogram body weight (mg/kg).

The compounds of formula (I) and pharmaceutically acceptable salts thereof may be used on their own but will generally be administered in the form of a pharmaceutical composition in which the formula (I) compound/salt (active ingredient) is in association with a pharmaceutically acceptable adjuvant, diluent or carrier.

Conventional procedures for the selection and preparation of suitable pharmaceutical formulations are described in, for example, "Pharmaceuticals—The Science of Dosage Form Designs", M. E. Aulton, Churchill Livingstone, 1988.

Pharmaceutically acceptable adjuvants, diluents or carriers that may be used are those conventionally employed in the field of pharmaceutical formulation, and include, but are not limited to, sugars, sugar alcohols, starches, ion exchangers, alumina, aluminium stearate, lecithin, serum proteins, such as human serum albumin, buffer substances such as phosphates, glycerine, sorbic acid, potassium sorbate, partial glyceride mixtures of saturated vegetable fatty acids, water, salts or electrolytes, such as protamine sulphate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions may be administered orally, parenterally, by inhalation spray, rectally, nasally, buccally, vaginally or via an implanted reservoir. Oral administration is preferred. The pharmaceutical compositions may contain any conventional non-toxic pharmaceutically acceptable adjuvants, diluents or carriers. The term parenteral as used herein includes subcutaneous, intracutaneous, intravenous, intramuscular, intra-articular, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. The suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable diluents and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent.

The pharmaceutical compositions may be orally administered in any orally acceptable dosage form including, but not limited to, capsules, tablets, powders, granules, and aqueous suspensions and solutions. These dosage forms are prepared according to techniques well-known in the art of pharmaceutical formulation. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavouring and/or colouring agents may be added.

The pharmaceutical compositions may also be administered in the form of suppositories for rectal administration. These compositions can be prepared by mixing the active ingredient with a suitable non-irritating excipient which is solid at room temperature but liquid at the rectal temperature and therefore will melt in the rectum to release the active ingredient. Such materials include, but are not limited to, cocoa butter, beeswax and polyethylene glycols.

The pharmaceutical compositions may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilising or dispersing agents known in the art.

Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The compounds of formula (I) and pharmaceutically acceptable salts thereof as defined above may also be administered in conjunction with other therapeutic agents used for the treatment of the above conditions as will be known to the person skilled in the art.

The present invention will now be further explained by reference to the following illustrative examples.

The methods used for synthesis of the compounds of formula (I) are illustrated by the general schemes below and the preparative examples that follow. The starting materials and reagents used in preparing these compounds are available from commercial suppliers. These general schemes are merely illustrative of methods by which the compounds of formula (I) can be synthesised, and various modifications to these schemes can be made and will be suggested to one skilled in the art having referred to this disclosure.

Nuclear magnetic resonance (NMR) spectra were recorded at 400 MHz; the chemical shifts (δ) are reported in parts per million. Spectra were recorded using a Bruker 400 Avance instrument fitted with a 5 mm BBFO probe or DUL probe. Instrument control was by Bruker TopSpin 2.1 software, unless stated otherwise.

Purity was assessed using UPLC with UV (photodiode array) detection over a wide range of wavelengths, normally 220-450 nm, using a Waters Acquity UPLC system equipped with Acquity UPLC BEH or HSS C18 columns (2.1 mm id×50 mm long) operated at 50 or 60° C. Mobile phases typically consisted of acetonitrile or methanol mixed with water containing either 0.05% formic acid or 0.025% ammonia. Mass spectra were recorded with a Waters SQD single quadrupole mass spectrometer using atmospheric pressure ionisation, unless stated otherwise.

Compounds were purified using normal phase chromatography on silica or alumina, or by reverse phase chromatographic methods, using Biotage or Isolute KPNH Cartridge, SCX cartridge and SCX-2 solid phase extraction cartridges.

Preparative HPLC was performed using an Agilent Technologies 1100 Series system or a Waters autopurification LC/MS system typically using Waters 19 mm id×100 mm long C18 columns such as XBridge or SunFire 5 μm materials at room temperature. Mobile phases typically consisted of acetonitrile or methanol mixed with water containing either 0.1% formic acid or 0.1% ammonia, unless stated otherwise.

Room temperature in the following schemes means the temperature ranging from 20° C. to 25° C.

The following abbreviations are used in the Examples:
n-BuLi n-Butyllithium
DCM Dichloromethane
DMSO Dimethyl sulfoxide
$d_6$-DMSO Deuterated dimethyl sulfoxide
EtOAc Ethyl acetate
$H_2O$ Water
HCl Hydrochloric acid
HPLC High performance liquid chromatography
LCMS Liquid chromatography-mass spectrometry
MeOH Methanol
MS Mass spectrum
NaOH Sodium hydroxide
$Na_2SO_4$ Sodium sulphate
NMR Nuclear magnetic resonance
THF Tetrahydrofuran

1. INTERMEDIATES

Intermediate 1:
3,5-Dimethyl-1H-pyrazole-4-sulfonyl chloride

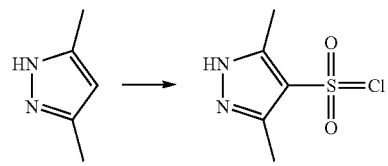

3,5-Dimethyl-1H-pyrazole (3.0 g, 1.0 eq) dissolved in chloroform (5 mL) was added dropwise to a solution of chlorosulfonic acid (19.95 g, 5.5 eq.) in chloroform (20 mL) under a nitrogen atmosphere at 0° C. with continuous stirring. The reaction was heated at 60° C. for 15 hours under continuous stirring. The reaction was cooled to room temperature and thionyl chloride (4.0 g, 1.1 eq) was gradually added. The reaction was heated at 60° C. for a further 2 hours. The reaction was cooled to room temperature and added to a stirred mixture of dichloromethane (50 mL) and ice cold water (70 mL). The organic layer was separated and the aqueous layer was extracted with dichloromethane (2×70 mL). The combined organic layer was dried over sodium sulfate and evaporated under vacuum to obtain the title compound, 3,5-dimethyl-1H-pyrazole-4-sulfonyl chloride (2.0 g, 42%), as a white solid.

$^1$H NMR (400 MHz, DMSO-$d_6$) δ ppm 2.40 (s, 6H)
MS ES$^+$: 195

Intermediate 2
3-Cyclopropyl-5-methyl-1H-pyrazole-4-sulfonyl chloride

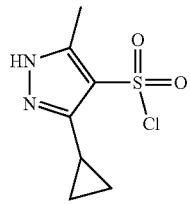

Hydrazine hydrate (7.93 g, 0.158 mol) was added to a solution of 1-cyclopropyl-1,3-butanedione (10 g, 0.079 mol) in ethanol (100 mL) and the reaction was heated to reflux for two hours then concentrated to afford 5-cyclopropyl-3-methyl-1H-pyrazole (9.59 g, 98% yield). This was reacted with chlorosulfonic acid as described in the preparation of 3,5-dimethyl-1H-pyrazole-4-sulfonyl chloride (Intermediate 1) to afford 5-cyclopropyl-3-methyl-1H-pyrazole-4-sulfonyl chloride.

Intermediate 3: tert-Butyl 4-(4-chloro-3-fluorobenzylidene)piperidine-1-carboxylate

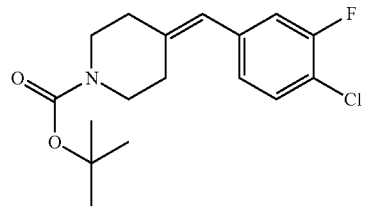 [SMILES: CC(C)(C)OC(=O)N1CCC(=Cc2ccc(Cl)c(F)c2)CC1]

A suspension of triphenylphosphine (2.347 g, 8.95 mmol) and 4-(bromomethyl)-1-chloro-2-fluorobenzene (2 g, 8.95 mmol) in ether (25 mL) was stirred at room temperature overnight. The suspension was concentrated to give (4-chloro-3-fluorobenzyl)-triphenylphosphonium bromide (quantitative) as a white solid that was used crude. Butyl lithium (1.6 M in hexanes) (6.03 mL, 9.65 mmol) was added slowly to a suspension of (4-chloro-3-fluorobenzyl)triphenylphosphonium bromide (4.26 g, 8.77 mmol) in THF (40 mL) under inert atmosphere at 0° C. The resulting suspension was stirred at 0° C. for 15 minutes, then warmed to room temperature for two hours. tert-Butyl 4-oxopiperidine-1-carboxylate (1.922 g, 9.65 mmol) as a solution in THF (5 mL) was added and the suspension was stirred at room temperature overnight. Petroleum ether was added, the precipitate (O=PPh3) was filtered and the filtrate concentrated. The crude product was purified by silica chromatography eluted with 0-100% DCM/petroleum ether to give tert-butyl 4-(4-chloro-3-fluorobenzylidene)piperidine-1-carboxylate (2.03 g, 6.23 mmol, 71% yield) as a colourless oil that solidified on standing.

$^1$H NMR (400 MHz, DMSO-d$_6$) δ ppm 1.42 (s, 9H) 2.28-2.30 (m, 2H) 2.39-2.40 (m, 2H) 3.27-3.34 (m, 2H) 3.36-3.47 (m, 2H) 6.35 (s, 1H) 7.06-7.13 (m, 1H) 7.25-7.28 (m, 1H) 7.51-7.55 (m, 1H)

Intermediate 4:
4-(4-Chloro-3-fluorobenzyl)piperidine hydrochloride

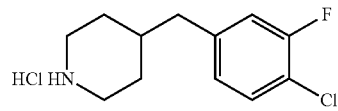

A flask charged with tert-butyl 4-(4-chloro-3-fluorobenzylidene)piperidine-1-carboxylate (2.03 g, 6.23 mmol, Intermediate 3) and platinum(IV)oxide (0.141 g, 0.623 mmol) was evacuated and flushed with argon three times. The flask was evacuated again and ethanol (20 mL) and ethyl acetate (20 mL) were added, then the suspension stirred under an atmosphere of hydrogen for two hours. The suspension was filtered through diatomaceous earth and the filtrate concentrated to give tert-butyl 4-(4-chloro-3-fluorobenzyl)piperidine-1-carboxylate (2.01 g, 6.13 mmol, 98% yield) as a yellow oil that was used without further purification. Hydrogen chloride (4M in dioxane) (3.05 mL, 12.20 mmol) was added to a solution of tert-butyl 4-(4-chloro-3-fluorobenzyl)piperidine-1-carboxylate (2 g, 6.10 mmol) in methanol (20 mL) and stirred overnight. The solution was concentrated and azeotroped with toluene to give 4-(4-chloro-3-fluorobenzyl)piperidine hydrochloride (1.56 g, 5.91 mmol, 97% yield) as a white solid.

$^1$H NMR (400 MHz, DMSO-d$_6$) δ ppm 1.28-1.44 (m, 2H) 1.60-1.73 (m, 2H) 1.74-1.88 (m, 1H) 2.54-2.60 (m, 2H) 2.69-2.86 (m, 2H) 3.15-3.25 (m, 2H) 7.05-7.12 (m, 1H) 7.24-7.32 (m, 1H) 7.46-7.54 (m, 1H) 8.80 (br. s., 1H) 9.06 (br. s., 1H)

Intermediate 5: Methyl 2-(4-chlorophenyl)-2-(piperidin-4-ylidene)acetate hydrochloride

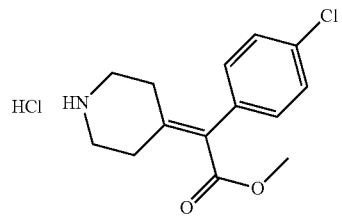 [SMILES: Cl ; COC(=O)C(=C1CCNCC1)c1ccc(Cl)cc1]

Step (i): tert-Butyl 4-(1-(4-chlorophenyl)-2-methoxy-2-oxoethyl)-4-hydroxypiperidine-1-carboxylate

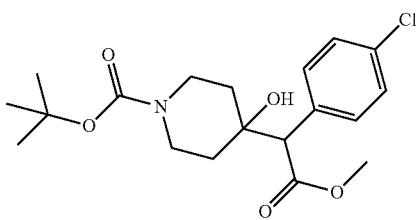 [SMILES: COC(=O)C(c1ccc(Cl)cc1)C1(O)CCN(C(=O)OC(C)(C)C)CC1]

A flask was charged with nitrogen and methyl 2-(4-chlorophenyl)acetate (2 g, 13.19 mmol) in tetrahydrofuran to give a colourless solution cooled to −78° C. n-Butyl lithium was added dropwise over 20 mins via a syringe pump and stirred for 30 minutes. tert-Butyl 4-oxopiperidine-1-carboxylate (2.63 g, 13.19 mmol) in THF was added dropwise via a syringe pump over 20 mins and stirred for a further 2.5 hours. While still cold the reaction was quenched with NH$_4$Cl and allowed to warm to room temperature overnight. The organic phase was separated, dried and evaporated to leave an oil. The crude product was purified by column chromatography on silica, eluted with EtOAc/petroleum ether 0-30% to afford the product as an oil (2.77 g, 60%).

Step (ii): tert-Butyl 4-(1-(4-chlorophenyl)-2-methoxy-2-oxoethylidene)piperidine-1-carboxylate

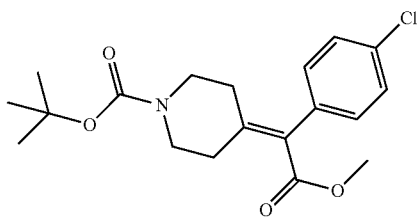 [SMILES: COC(=O)C(=C1CCN(C(=O)OC(C)(C)C)CC1)c1ccc(Cl)cc1]

A flask was charged with tert-butyl 4-(1-(4-chlorophenyl)-2-methoxy-2-oxoethyl)-4-hydroxypiperidine-1-carboxylate (from step (i), 1.29 g, 3.68 mmol) in pyridine (2 mL) to give a colourless solution. Thionyl chloride (1.334 mL, 18.38 mmol) was added and the reaction stirred for 10 mins, then evaporated to dryness. The crude product was purified by column chromatography on silica, eluted with 10-50% Hexane/EtOAc to afford the product (0.78 g, 58%).

Step (iii): Methyl 2-(4-chlorophenyl)-2-(piperidin-4-ylidene)acetate hydrochloride

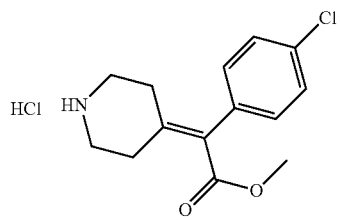 [SMILES: Cl ; COC(=O)C(=C1CCNCC1)c1ccc(Cl)cc1]

tert-Butyl 4-(1-(4-chlorophenyl)-2-methoxy-2-oxoethylidene)piperidine-1-carboxylate (from step (ii), 0.78 g, 2.14 mmol) was treated with 4N HCl in dioxane and stirred for one hour then evaporated to leave a white solid, (0.21 g, 33%).

MS: ES+ 266

Intermediate 6: 2-(4-Chlorophenyl)-2-(piperidin-4-ylidene)acetonitrile hydrochloride

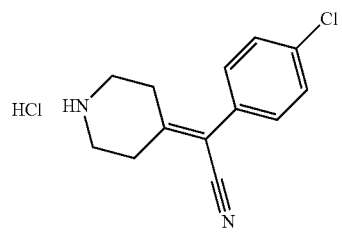 [SMILES: Cl ; N#CC(=C1CCNCC1)c1ccc(Cl)cc1]

Prepared in a similar manner to methyl 2-(4-chlorophenyl)-2-(piperidin-4-ylidene)acetate hydrochloride (Intermediate 5) using 2-(4-chlorophenyl) acetonitrile.

MS: ES+ 233

Intermediate 7: 2-(2,6-Difluorophenyl)-2-(piperidin-4-ylidene)acetonitrile hydrochloride

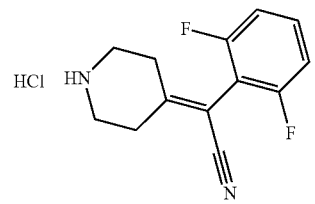 [SMILES: Cl ; N#CC(=C1CCNCC1)c1c(F)cccc1F]

Prepared in a similar manner to methyl 2-(4-chlorophenyl)-2-(piperidin-4-ylidene)acetate hydrochloride (Intermediate 5) using 2-(2,6-difluorophenyl) acetonitrile.

MS: ES+ 235

Intermediate 8: 2-(4-Chloro-2-fluorophenyl)-2-(piperidin-4-ylidene)acetonitrile hydrochloride

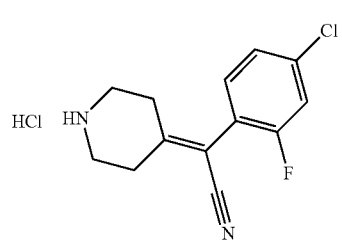 [SMILES: Cl ; N#CC(=C1CCNCC1)c1ccc(Cl)cc1F]

Prepared in a similar manner to methyl 2-(4-chlorophenyl)-2-(piperidin-4-ylidene)acetate hydrochloride (Intermediate 5) using 2-(2-fluoro-4-chlorophenyl) acetonitrile.

MS: ES+ 251

Intermediate 9: 1,5-Dimethyl-3-(trifluoromethyl)-1H-pyrazole-4-sulfonyl chloride

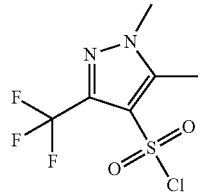

Prepared in a similar manner to 3-cyclopropyl-5-methyl-1H-pyrazole-4-sulfonyl chloride (Intermediate 2) from 1,1,1-trifluoropentane-2,4-dione and methylhydrazine.

$^1$H NMR (400 MHz, CDCl$_3$) δ ppm 2.63 (s, 3H), 3.91 (s, 3H)

Intermediate 10: 2-(Piperidin-4-ylidene)-2-(4-(trifluoromethoxy)phenyl)-acetonitrile hydrochloride

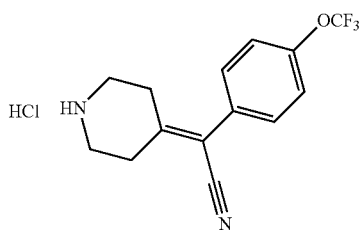 [SMILES: Cl ; N#CC(=C1CCNCC1)c1ccc(OC(F)(F)F)cc1]

Prepared in a similar manner to methyl 2-(4-chlorophenyl)-2-(piperidin-4-ylidene)acetate hydrochloride (Intermediate 5) using 2-(4-(trifluoromethoxy)phenyl)acetonitrile.

MS: ES+ 283

Intermediate 11: 2-(4-Chlorophenyl)-2-(3-methylpiperidin-4-ylidene)acetonitrile hydrochloride

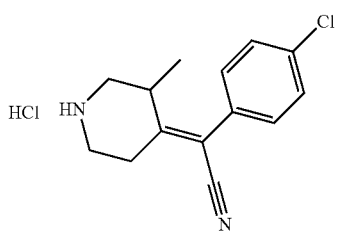 [SMILES: Cl ; CC1CNCC/C1=C(\C#N)c1ccc(Cl)cc1]

Prepared in a similar manner to methyl 2-(4-chlorophenyl)-2-(piperidin-4-ylidene)acetate hydrochloride (Intermediate 5) using 2-(4-chlorophenyl) acetonitrile and tert-butyl 3-methyl-4-oxopiperidine-1-carboxylate.

MS: ES+ 247

Intermediate 12: tert-Butyl 4-(1-(4-chlorophenyl)-1-hydroxyethyl)piperidine-1-carboxylate

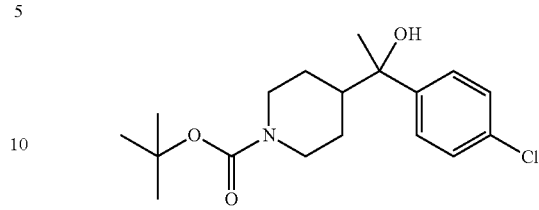

Di-tert-butyl dicarbonate (0.923 g, 4.23 mmol) was added to a solution of (4-chlorophenyl)(piperidin-4-yl)methanone hydrochloride (1 g, 3.84 mmol) and triethylamine (1.179 mL, 8.46 mmol) in methanol (20 mL) under nitrogen. The reaction was stirred at room temperature overnight. The suspension was concentrated in vacuo. The residue was taken up in ethyl acetate and water and the phases separated. The organic was washed with brine, dried (phase separator) and concentrated to give tert-butyl 4-(4-chlorobenzoyl)piperidine-1-carboxylate (1.22 g, 3.77 mmol, 98% yield) as a white solid.

$^1$H NMR (400 MHz, DMSO-d$_6$) δ ppm 1.33-1.46 (m, 11H) 1.72-1.81 (m, 2H) 2.83-3.00 (m, 2H) 3.62 (s, 1H) 3.92-4.02 (m, 2H) 7.58-7.65 (m, 2H) 7.98-8.04 (m, 2H).

Methylmagnesium bromide (3M in ether) (3.09 mL, 9.26 mmol) was added slowly to a solution of tert-butyl 4-(4-chlorobenzoyl)piperidine-1-carboxylate (0.5 g, 1.544 mmol) in THF (10 mL) at 0° C. under nitrogen. The reaction was stirred at room temperature for 2 hours. The reaction was quenched with 2M HCl and partitioned between ethyl acetate and 2M HCl. The phases were separated and the aqueous phase was extracted with ethyl acetate. The combined organics were washed with saturated brine, dried (phase separator) and concentrated in vacuo to afford tert-butyl 4-(1-(4-chlorophenyl)-1-hydroxyethyl)piperidine-1-carboxylate (0.481 g, 1.415 mmol, 92% yield) as a colourless oil. MS: ES– 338.

Intermediate 13: 4-(4-Chlorobenzylidene)piperidine hydrochloride

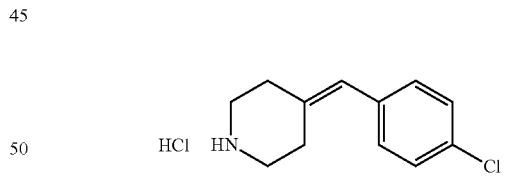

(4-Chlorobenzyl)triphenylphosphonium bromide (prepared in an analogous manner to (4-chloro-3-fluorobenzyl)triphenylphosphonium bromide described in the synthesis of Intermediate 3) (20 g, 42.8 mmol) was added to THF (200 mL) and n-BuLi (6.03 g, 94 mmol) added at 0° C. The reaction was stirred at room temperature for two hours. tert-Butyl 4-oxopiperidine-1-carboxylate (8.52 g, 42.8 mmol) was added and the reaction was stirred at room temperature overnight. The reaction mixture was poured onto saturated aqueous ammonium chloride solution and extracted with ethyl acetate. The combined organic layers were dried (Na$_2$SO$_4$), filtered and concentrated under reduced pressure. The crude product was purified by column chromatography on silica, eluted with 0-10% ethyl acetate/petroleum ether to afford tert-butyl 4-(4-chlorobenzylidene)

piperidine-1-carboxylate (7 g, 53%). Hydrogen chloride (4M in dioxane) (0.609 mL, 2.437 mmol) was added to a solution of tert-butyl 4-(4-chlorobenzylidene)piperidine-1-carboxylate (0.25 g, 0.812 mmol) in methanol (5 mL). The reaction was stirred at room temperature overnight. A further portion of hydrogen chloride (4M in dioxane) (0.609 mL, 2.437 mmol) was added and the solution stirred for three hours. The solution was concentrated and azeotroped with toluene to give 4-(4-chlorobenzylidene)piperidine hydrochloride (0.196 g, 0.803 mmol, 99% yield) as a white solid.
MS: ES+ 208

Intermediate 14:
4-((4-Chlorophenyl)fluoromethylene)piperidine hydrochloride

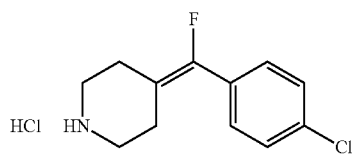 [SMILES: Cl ; FC(=C1CCNCC1)c1ccc(Cl)cc1]

Diethyl ((4-chlorophenyl)fluoromethyl)phosphonate (prepared as described by Azizi et. al. Phosphorus, Sulfur and Silicon and the Related Elements, 178(6), 1255-1259; 2003 followed by Blackburn et. al. Journal of the Chemical Society, Perkin Transactions 1: Organic and Bio-Organic Chemistry (1972-1999), (6), 913-17; 1986) (0.61 g, 2.173 mmol) and tert-butyl 4-oxopiperidine-1-carboxylate (0.433 g, 2.173 mmol) in THF (20 mL) at 0° C. was treated with sodium hydride (60% in mineral oil, 0.229 g, 4.78 mmol). The reaction mixture was allowed to reach room temperature and stirred for 18 hours, then quenched with water and evaporated. To the reaction mixture was added DCM/H$_2$O and the organic layer dried (phase separator) and concentrated in vacuo to yield an oil. The crude product was purified by column chromatography on silica, eluted with EtOAc/petroleum ether 0-50% to afford tert-butyl 4-((4-chlorophenyl)fluoromethylene)-piperidine-1-carboxylate (0.41 g, 58%).

$^1$H NMR (400 MHz, CD$_2$Cl$_2$) δ ppm 1.48 (s, 9H) 2.30-2.36 (m, 2H) 2.48-2.54 (m, 2H) 3.42-3.48 (m, 2H) 3.51-3.55 (m, 2H) 7.38-7.45 (m, 4H)

tert-Butyl 4-((4-chlorophenyl)fluoromethylene)piperidine-1-carboxylate (0.39 g, 1.19 mmol) was treated with 4N HCl in dioxane and stirred for one hour then evaporated to leave a white solid (quantitative) that was used without purification.
MS: ES+ 226

Intermediate 15: 4-((3-Chloro-4-fluorophenyl)fluoromethylene)piperidine hydrochloride

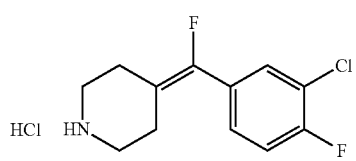 [SMILES: Cl ; FC(=C1CCNCC1)c1ccc(F)c(Cl)c1]

Prepared in a similar manner to 4-((4-chlorophenyl)fluoromethylene)piperidine hydrochloride (Intermediate 14).

Intermediate 16:
4-((2,4-Dichlorophenyl)fluoromethylene)piperidine hydrochloride

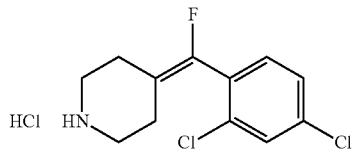 [SMILES: Cl ; FC(=C1CCNCC1)c1ccc(Cl)cc1Cl]

Prepared in a similar manner to 4-((4-chlorophenyl)fluoromethylene)piperidine hydrochloride (Intermediate 14).

Intermediate 17:
4-((3,4-Dichlorophenyl)fluoromethylene)piperidine hydrochloride

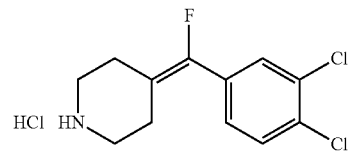 [SMILES: Cl ; FC(=C1CCNCC1)c1ccc(Cl)c(Cl)c1]

Prepared in a similar manner to 4-((4-chlorophenyl)fluoromethylene)piperidine hydrochloride (Intermediate 14).

Intermediate 18: 4-((4-Chloro-3-fluorophenyl)fluoromethylene)piperidine hydrochloride

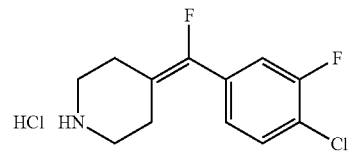 [SMILES: Cl ; FC(=C1CCNCC1)c1ccc(Cl)c(F)c1]

Prepared in a similar manner to 4-((4-chlorophenyl)fluoromethylene)piperidine hydrochloride (Intermediate 14).

Intermediate 19: 4-((4-Chloro-2-fluorophenyl)fluoromethylene)piperidine hydrochloride

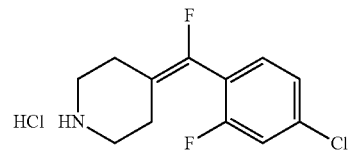 [SMILES: Cl ; FC(=C1CCNCC1)c1ccc(Cl)cc1F]

Prepared in a similar manner to 4-((4-chlorophenyl)fluoromethylene)piperidine hydrochloride (Intermediate 14).

Intermediate 20: 4-((2,4-Difluorophenyl)fluoromethylene)piperidine hydrochloride

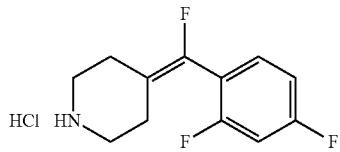 [SMILES: Cl ; FC(=C1CCNCC1)c1ccc(F)cc1F]

Prepared in a similar manner to 4-((4-chlorophenyl)fluoromethylene)piperidine hydrochloride (Intermediate 14).

Intermediate 21: 3-(Fluoro(piperidin-4-ylidene)methyl)quinoline hydrochloride

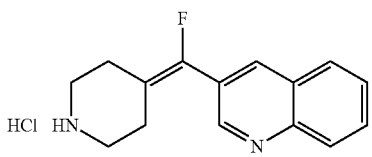 [SMILES: Cl ; FC(=C1CCNCC1)c1cnc2ccccc2c1]

Prepared in a similar manner to 4-((4-chlorophenyl)fluoromethylene)piperidine hydrochloride (Intermediate 14).

2. EXAMPLES

Example 1 4-(4-Chloro-3-fluorobenzyl)-1-((3-cyclopropyl-5-methyl-1H-pyrazol-4-yl)sulfonyl)piperidine

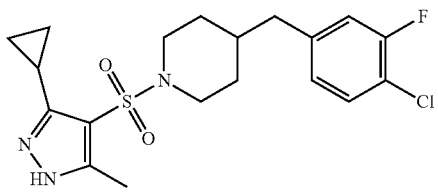 [SMILES: Cc1[nH]nc(C2CC2)c1S(=O)(=O)N1CCC(Cc2ccc(Cl)c(F)c2)CC1]

The title compound was prepared from 5-cyclopropyl-3-methyl-1H-pyrazole-4-sulfonyl chloride (Intermediate 2, 150 mg, 0.68 mmol) and 4-(4-chloro-3-fluorobenzyl)piperidine hydrochloride (Intermediate 4, 176 mg, 0.68 mmol). The reaction was stirred at room temperature for two hours. To the reaction mixture was added DCM/H$_2$O and the organic layer dried (phase separator) and concentrated in vacuo to yield an oil. The crude product was purified by column chromatography on silica, eluted with EtOAc/petroleum ether 0-100% to afford the title compound, 0.14 g, 50% yield.

$^1$H NMR (400 MHz, ACETONITRILE-d$_3$) δ ppm 0.58-0.77 (m, 3H) 0.97-1.12 (m, 2H) 1.27-1.40 (m, 1H) 1.41-1.49 (m, 2H) 1.71-1.76 (m, 3H) 2.06-2.15 (m, 4H) 2.28-2.36 (m, 2H) 3.43-3.51 (m, 2H) 6.72-6.78 (m, 1H) 6.81-6.87 (m, 1H) 7.12-7.18 (m, 1H) 10.89-11.03 (m, 1H)

MS: ES+ 412

Example 2 Methyl 2-(4-Chlorophenyl)-2-(1-((3,5-dimethyl-1H-pyrazol-4-yl)sulfonyl)piperidin-4-ylidene)acetate

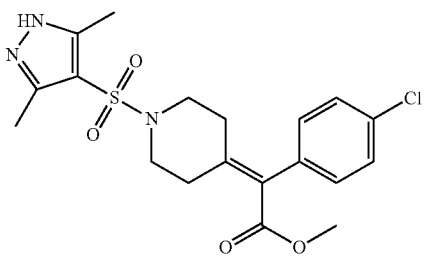 [SMILES: COC(=O)C(=C1CCN(S(=O)(=O)c2c(C)n[nH]c2C)CC1)c1ccc(Cl)cc1]

A flask was charged with nitrogen and methyl 2-(4-chlorophenyl)-2-(piperidin-4-ylidene)acetate hydrochloride (Intermediate 5, 210 mg, 0.790 mmol) in DCM (10 mL) to give a colourless solution. 3,5-Dimethyl-1H-pyrazole-4-sulfonyl chloride (Intermediate 1; 114 mg, 0.586 mmol) and triethylamine (0.330 mL, 2.371 mmol) were added. The reaction was stirred at room temperature for two hours. To the reaction mixture was added DCM/H$_2$O and the organic layer dried (phase separator) and concentrated in vacuo to yield an oil. The crude product was purified by column chromatography on silica, eluted with EtOAc/petroleum ether 0-100%, EtOAc/MeOH 0-20% to afford the title compound.

$^1$H NMR (400 MHz, DMSO-d$_6$) δ ppm 2.25-2.28 (m, 2H) 2.34 (S, 6H) 2.75-2.78 (m, 2H) 2.96-2.96 (m, 2H) 3.01-3.03 (s, 2H) 3.60 (s, 3H) 7.16-7.29 (m, 2H) 7.38-7.41 (m, 2H)

MS: ES+ 424

Example 3 2-(4-Chlorophenyl)-2-(1-((3,5-dimethyl-1H-pyrazol-4-yl)sulfonyl)piperidin-4-ylidene)acetonitrile

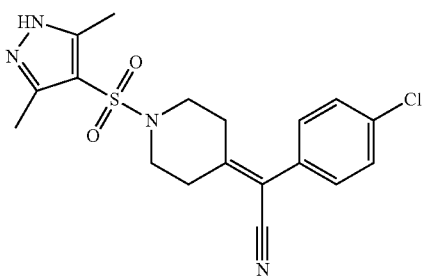 [SMILES: Cc1n[nH]c(C)c1S(=O)(=O)N1CCC(=C(C#N)c2ccc(Cl)cc2)CC1]

Prepared as described for methyl 2-(4-chlorophenyl)-2-(1-((3,5-dimethyl-1H-pyrazol-4-yl)sulfonyl)piperidin-4-ylidene)acetate (Example 2) from 3,5-dimethyl-1H-pyrazole-4-sulfonyl chloride (Intermediate 1, 0.32 g, 1.67 mmol) and 2-(4-chlorophenyl)-2-(piperidin-4-ylidene)acetonitrile hydrochloride (Intermediate 6, 0.39 g, 1.67 mmol) to give the title compound (0.49 g, 76%).

$^1$H NMR (400 MHz, DMSO-d$_6$) δ ppm 2.25-2.38 (m, 8H) 2.75-2.78 (m, 2H) 3.01-3.03 (s, 2H) 3.18-3.20 (m, 2H) 7.32-7.36 (m, 2H) 7.52-7.56 (m, 2H) 13.0 (s, 1H)

MS: ES+ 391

Example 4 2-(2,6-Difluorophenyl)-2-(1-((3,5-dimethyl-1H-pyrazol-4-yl)sulfonyl)piperidin-4-ylidene)acetonitrile

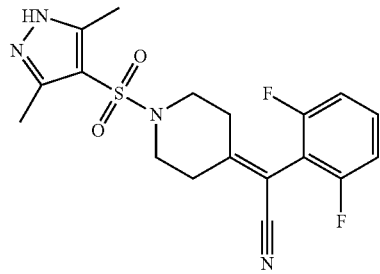 [SMILES: Cc1n[nH]c(C)c1S(=O)(=O)N1CCC(=C(C#N)c2c(F)cccc2F)CC1]

Prepared as described for methyl 2-(4-chlorophenyl)-2-(1-((3,5-dimethyl-1H-pyrazol-4-yl)sulfonyl)piperidin-4-ylidene)acetate (Example 2) from 3,5-dimethyl-1H-pyrazole-4-sulfonyl chloride (Intermediate 1, 0.12 g, 0.58 mmol) and 2-(2,6-difluorophenyl)-2-(piperidin-4-ylidene)acetonitrile hydrochloride (Intermediate 7, 0.21 g, 0.89 mmol) to give the title compound (0.23 g, 67%).

$^1$H NMR (400 MHz, DMSO-$d_6$) δ ppm 2.25-2.38 (m, 8H) 2.82-2.90 (m, 2H) 2.93-3.03 (m, 2H) 3.18-3.20 (m, 2H) 7.25-7.33 (m, 2H) 7.58-7.63 (m, 1H) 13.0 (s, 1H)

MS: ES+ 393

Example 5 2-(4-Chloro-2-fluorophenyl)-2-(1-((3,5-dimethyl-1H-pyrazol-4-yl)sulfonyl)piperidin-4-ylidene)acetonitrile

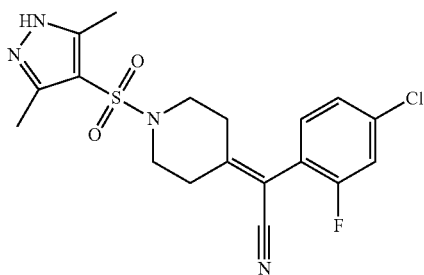 [SMILES: Cc1n[nH]c(C)c1S(=O)(=O)N1CCC(=C(C#N)c2ccc(Cl)cc2F)CC1]

Prepared as described for methyl 2-(4-chlorophenyl)-2-(1-((3,5-dimethyl-1H-pyrazol-4-yl)sulfonyl)piperidin-4-ylidene)acetate (Example 2) from 3,5-dimethyl-1H-pyrazole-4-sulfonyl chloride (Intermediate 1, 0.3 g, 1.54 mmol) and 2-(4-chloro-2-fluorophenyl)-2-(piperidin-4-ylidene)acetonitrile hydrochloride (Intermediate 8, 0.44 g, 1.54 mmol) to give the title compound (0.54 g, 86%).

$^1$H NMR (400 MHz, DMSO-$d_6$) δ ppm 2.25-2.38 (m, 8H) 2.80-2.88 (m, 2H) 2.96-3.03 (m, 2H) 3.18-3.20 (m, 2H) 7.41-7.48 (m, 2H) 7.60-7.63 (m, 1H) 13.0 (s, 1H)

MS: ES+ 409

Example 6 2-(4-Chlorophenyl)-2-(1-((3,5-diethyl-1H-pyrazol-4-yl)sulfonyl)piperidin-4-ylidene)acetonitrile

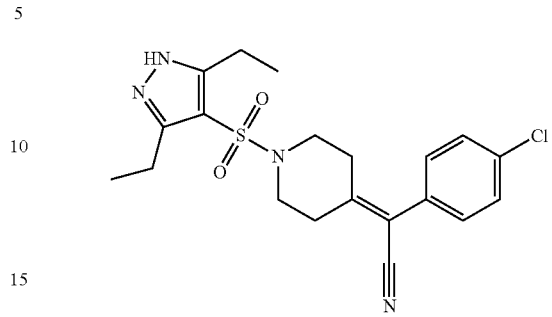

A solution of 3,5-heptanedione (12.5 g, 97.5 mmol) in ethanol (50 mL) was treated dropwise with hydrazine hydrate (60%, 5.72 g, 107 mmol) whilst cooling in an ice bath. The reaction was stirred for 1.5 hours at room temperature. The reaction was concentrated under reduced pressure. The reaction mixture was partitioned between DCM and brine, the aqueous layer was extracted with DCM. The combined organic layers were dried (Na$_2$SO$_4$), filtered and concentrated under reduced pressure to afford 3,5-diethyl-1H-pyrazole that was used crude. 3,5-diethyl-1H-pyrazole (6.0 g, 0.048 mol) was added dropwise to chlorosulfonic acid (30.9 g, 17.7 mL, 0.265 mol) at 0° C. with stirring. The reaction was heated to 80° C. for 30 minutes. The reaction was cooled and thionyl chloride (6.32 g, 3.8 mL, 53.1 mol) was added dropwise. The reaction was heated to 65° C. for 4 hours. The reaction mixture was cooled to room temperature and carefully poured onto ice (100 g) with stirring. The resultant solid was filtered and dried under vacuum to afford 3,5-diethyl-1H-pyrazole-4-sulfonyl chloride as a brown solid (9.15 g, 85% yield).

The title compound was prepared as described for methyl 2-(4-chlorophenyl)-2-(1-((3,5-dimethyl-1H-pyrazol-4-yl)sulfonyl)piperidin-4-ylidene)acetate (Example 2) from 3,5-diethyl-1H-pyrazole-4-sulfonyl chloride (0.11 g, 0.47 mmol) and 2-(4-chlorophenyl)-2-(piperidin-4-ylidene)acetonitrile hydrochloride (Intermediate 6, 0.1 g, 0.47 mmol) in the following yield: 0.072 g (38%).

$^1$H NMR (400 MHz, DMSO-$d_6$) δ ppm 1.15-1.21 (m, 6H) 2.40-2.50 (m, 2H) 2.71-2.78 (m, 2H) 2.78-2.82 (m, 4H) 2.98-3.03 (m, 2H) 3.18-3.22 (m, 2H) 7.34-7.40 (m, 2H) 7.50-7.62 (m, 2H) 13.0 (s, 1H)

MS: ES+ 419

Example 7 2-(4-Chlorophenyl)-2-(1-((1,5-dimethyl-3-(trifluoromethyl)-1H-pyrazol-4-yl)sulfonyl)piperidin-4-ylidene)acetonitrile

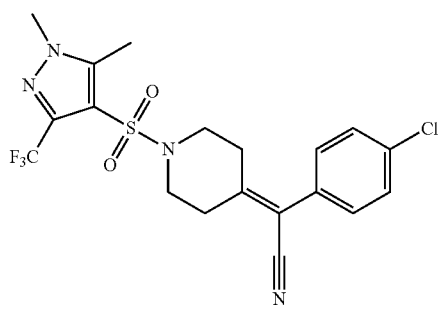 [SMILES: Cc1c(S(=O)(=O)N2CCC(=C(C#N)c3ccc(Cl)cc3)CC2)c(C(F)(F)F)nn1C]

Prepared as described for methyl 2-(4-chlorophenyl)-2-(1-((3,5-dimethyl-1H-pyrazol-4-yl)sulfonyl)piperidin-4-ylidene)acetate (Example 2) from 1,5-dimethyl-3-(trifluoromethyl)-1H-pyrazole-4-sulfonyl chloride (Intermediate 9, 0.1 g, 0.47 mmol) and 2-(4-chlorophenyl)-2-(piperidin-4-ylidene)acetonitrile hydrochloride (Intermediate 6, 0.12 g, 0.47 mmol) to give the title compound (0.11 g, 50%).

$^1$H NMR (400 MHz, DMSO-$d_6$) δ ppm 2.42-2.50 (m, 5H) 2.75-2.80 (m, 2H) 3.12-3.18 (m, 2H) 3.30-3.40 (m, 2H) 3.85 (s, 3H) 7.42-7.48 (m, 2H) 7.52-7.60 (m, 2H)

MS: ES+ 459

Example 8 2-(2,6-Difluorophenyl)-2-(1-((1,3,5-trimethyl-1H-pyrazol-4-yl)sulfonyl)piperidin-4-ylidene)acetonitrile

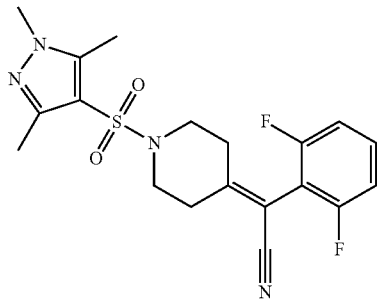 [SMILES: Cc1nn(C)c(C)c1S(=O)(=O)N1CCC(=C(C#N)c2c(F)cccc2F)CC1]

Prepared as described for methyl 2-(4-chlorophenyl)-2-(1-((3,5-dimethyl-1H-pyrazol-4-yl)sulfonyl)piperidin-4-ylidene)acetate (Example 2) from 1,3,5-trimethyl-1H-pyrazole-4-sulfonyl chloride (0.14 g, 0.58 mmol) and 2-(2,6-difluorophenyl)-2-(piperidin-4-ylidene)acetonitrile hydrochloride (Intermediate 7, 0.11 g, 0.89 mmol) to give the title compound (0.05 g, 26%).

$^1$H NMR (400 MHz, DMSO-$d_6$) δ ppm 2.20 (s, 3H) 2.20-2.34 (m, 2H) 2.40 (s, 3H) 2.82-2.90 (m, 2H) 2.98-3.00 (m, 2H) 3.18-3.24 (m, 2H) 3.70 (s, 3H) 7.24-7.30 (m, 2H) 7.58-7.63 (m, 1H)

MS: ES+ 407

Example 9 2-(1-((3,5-Dimethyl-1H-pyrazol-4-yl)sulfonyl)piperidin-4-ylidene)-2-(4-(trifluoromethoxy)phenyl)acetonitrile

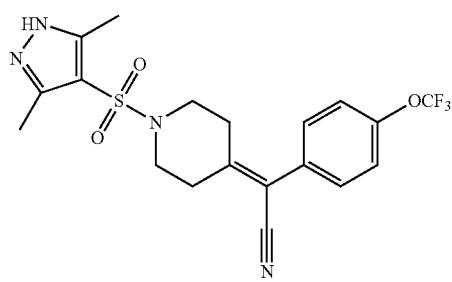 [SMILES: Cc1n[nH]c(C)c1S(=O)(=O)N1CCC(=C(C#N)c2ccc(OC(F)(F)F)cc2)CC1]

Prepared as described for methyl 2-(4-chlorophenyl)-2-(1-((3,5-dimethyl-1H-pyrazol-4-yl)sulfonyl)piperidin-4-ylidene)acetate (Example 2) from 3,5-dimethyl-1H-pyrazole-4-sulfonyl chloride (Intermediate 1, 0.12 g, 0.62 mmol) and 2-(piperidin-4-ylidene)-2-(4-(trifluoromethoxy)phenyl) acetonitrile hydrochloride (Intermediate 10, 0.2 g, 0.62 mmol) to give the title compound (0.14 g, 50%).

$^1$H NMR (400 MHz, DMSO-$d_6$) δ ppm 2.25-2.32 (m, 6H) 2.45-2.30 (m, 2H) 2.80-2.85 (m, 2H) 2.98-3.05 (m, 2H) 3.18-3.22 (m, 2H) 7.42-7.52 (m, 4H) 13.0 (s, 1H)

MS: ES+ 441

Example 10 2-(4-Chlorophenyl)-2-(1-((3,5-dimethyl-1H-pyrazol-4-yl)sulfonyl)-3-methylpiperidin-4-ylidene)acetonitrile

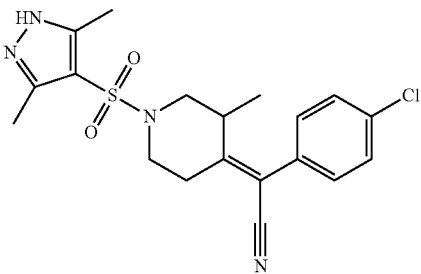 [SMILES: Cc1n[nH]c(C)c1S(=O)(=O)N1CC/C(=C(\C#N)c2ccc(Cl)cc2)C(C)C1]

Prepared as described for methyl 2-(4-chlorophenyl)-2-(1-((3,5-dimethyl-1H-pyrazol-4-yl)sulfonyl)piperidin-4-ylidene)acetate (Example 2) from 3,5-dimethyl-1H-pyrazole-4-sulfonyl chloride (Intermediate 1, 0.085 g, 0.43 mmol) and 2-(4-chlorophenyl)-2-(3-methylpiperidin-4-ylidene)acetonitrile hydrochloride (Intermediate 11, 0.12 g, 0.43 mmol) to give the title compound (0.055 g, 31%).

$^1$H NMR (400 MHz, DMSO-$d_6$) δ ppm 1.20 (m, 3H) 2.20-2.25 (m, 2H) 2.42-2.60 (m, 3H) 2.60 (s, 6H) 3.18-3.22 (m, 2H) 7.25-7.60 (m, 4H) 13 (s, 1H)

MS: ES+ 405

Example 11 4-(4-Chloro-2-fluorobenzylidene)-1-((3,5-dimethyl-1H-pyrazol-4-yl)sulfonyl)piperidine

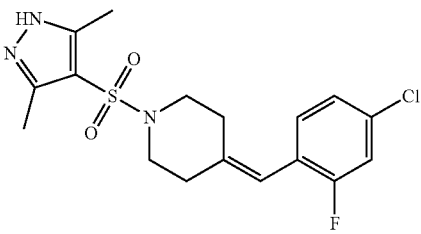 [SMILES: Cc1n[nH]c(C)c1S(=O)(=O)N1CCC(=Cc2ccc(Cl)cc2F)CC1]

tert-Butyl 4-(4-chloro-2-fluorobenzylidene)piperidine-1-carboxylate was prepared as described for tert-butyl 4-(4-chloro-3-fluorobenzylidene)piperidine-1-carboxylate (Intermediate 3) from 4-(bromomethyl)-1-chloro-3-fluorobenzene. Hydrogen chloride (4M in dioxane) (0.384 mL, 1.535 mmol) was added to a suspension of tert-butyl 4-(4-chloro-2-fluorobenzylidene)piperidine-1-carboxylate (0.25 g, 0.767 mmol) in methanol (5 mL). The reaction was stirred at room temperature overnight. The solution was concentrated in vacuo and azeotroped with toluene to give 4-(4-chloro-2-fluorobenzylidene)piperidine hydrochloride (0.2 g, 0.763 mmol, 99% yield) as a white solid. The title compound was prepared as described for 4-(4-chloro-3-fluorobenzyl)-1-((3-cyclopropyl-5-methyl-1H-pyrazol-4-yl)sulfonyl)piperidine (Example 1) from 3,5-dimethyl-1H- pyrazole-4-sulfonyl chloride (Intermediate 1) and 4-(4-chloro-2-fluorobenzylidene)piperidine hydrochloride.

¹H NMR (400 MHz, DMSO-d₆) δ ppm 2.25-2.39 (m, 8H) 2.41-2.47 (m, 2H) 2.89-2.99 (m, 2H) 3.00-3.09 (m, 2H) 6.22 (s, 1H) 7.19-7.32 (m, 2H) 7.37-7.45 (m, 1H) 13.05 (br. s., 1H)

MS: ES+ 384

Example 12 4-(4-Chloro-2-fluorobenzylidene)-1-((1,3,5-trimethyl-1H-pyrazol-4-yl)sulfonyl)piperidine

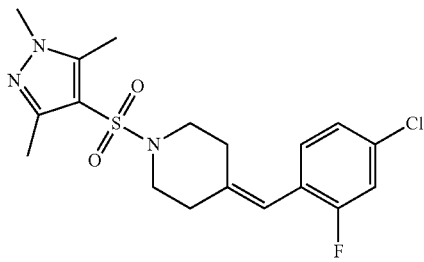 [SMILES: Cc1nn(C)c(C)c1S(=O)(=O)N1CCC(=Cc2ccc(Cl)cc2F)CC1]

Prepared as described for 4-(4-chloro-2-fluorobenzylidene)-1-((3,5-dimethyl-1H-pyrazol-4-yl)sulfonyl)piperidine (Example 11) using 1,3,5-trimethyl-1H-pyrazole-4-sulfonyl chloride.

¹H NMR (400 MHz, DMSO-d₆) δ ppm 2.24 (s, 3H) 2.33-2.41 (m, 5H) 2.42-2.48 (m, 2H) 2.90-2.96 (m, 2H) 3.00-3.07 (m, 2H) 3.70 (s, 3H) 6.22 (s, 1H) 7.23-7.32 (m, 2H) 7.38-7.44 (m, 1H)

MS: ES+ 398

Example 13 4-(1-(4-Chlorophenyl)ethylidene)-1-((3,5-dimethyl-1H-pyrazol-4-yl)sulfonyl)piperidine

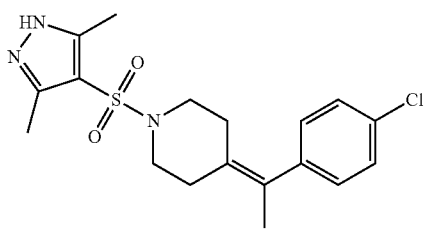 [SMILES: CC(=C1CCN(S(=O)(=O)c2c(C)n[nH]c2C)CC1)c1ccc(Cl)cc1]

p-Toluenesulfonic acid monohydrate (0.963 g, 5.06 mmol) was added to a solution of tert-butyl 4-(1-(4-chlorophenyl)-1-hydroxyethyl)piperidine-1-carboxylate (Intermediate 12, 0.43 g, 1.265 mmol) in toluene (15 ml) under nitrogen. Magnesium sulfate was added and the reaction was heated to reflux for 5 hours then cooled overnight. The reaction was quenched with 2M NaOH and the mixture was partitioned between ethyl acetate and water. The phases were separated and the aqueous extracted with ethyl acetate (2×200 ml). The combined organics were washed with saturated brine (2×100 ml), dried (phase separator) and concentrated in vacuo to afford 4-(1-(4-chlorophenyl)ethylidene)piperidine 4-methylbenzenesulfonate, which was taken on without further purification.

MS: ES+ 222

Triethylamine (0.386 ml, 2.77 mmol) was added to a suspension of 4-(1-(4-chlorophenyl)ethylidene)piperidine 4-methylbenzenesulfonate (0.364 g, 0.924 mmol) and 3,5-dimethyl-1H-pyrazole-4-sulfonyl chloride (Intermediate 1, 0.216 g, 1.109 mmol) in DCM (10 ml). The reaction was stirred at room temperature for 4 hours. The mixture was diluted with DCM, washed with water (1×25 ml), dried (phase separator) and concentrated in vacuo. The crude product was purified by column chromatography on silica, eluted with 0-100% ethyl acetate/petroleum ether. LCMS/NMR shows mixture of products. The crude product was purified by reverse phase preparative HPLC eluted with acetonitrile/water (with 0.1% ammonia) to afford 4-(1-(4-chlorophenyl)ethylidene)-1-((3,5-dimethyl-1H-pyrazol-4-yl)sulfonyl)piperidine (0.057 g, 0.150 mmol, 16.24% yield) as a white solid.

¹H NMR (400 MHz, DMSO-d₆) δ ppm 1.90 (s, 3H) 2.07-2.17 (m, 2H) 2.30 (br. s., 6H) 2.42-2.48 (m, 2H) 2.78-2.87 (m, 2H) 2.97-3.03 (m, 2H) 7.07-7.17 (m, 2H) 7.32-7.40 (m, 2H) 13.04 (br. s., 1H)

MS: ES+ 380

Example 14 4-(4-Chlorobenzylidene)-1-((3,5-dimethyl-1H-pyrazol-4-yl)sulfonyl)piperidine

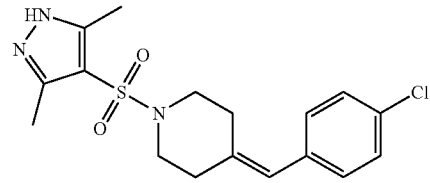 [SMILES: Cc1n[nH]c(C)c1S(=O)(=O)N1CCC(=Cc2ccc(Cl)cc2)CC1]

Prepared as described for 4-(4-chloro-3-fluorobenzyl)-1-((3-cyclopropyl-5-methyl-1H-pyrazol-4-yl)sulfonyl)piperidine (Example 1) from 3,5-dimethyl-1H-pyrazole-4-sulfonyl chloride (Intermediate 1) and 4-(4-Chlorobenzylidene)piperidine hydrochloride (Intermediate 13).

¹H NMR (400 MHz, DMSO-d₆) δ ppm 2.30 (br. s., 6H) 2.36-2.43 (m, 2H) 2.45-2.48 (m, 2H) 2.90-2.97 (m, 2H) 3.00-3.06 (m, 2H) 6.32 (s, 1H) 7.17-7.23 (m, 2H) 7.33-7.40 (m, 2H) 13.03 (br. s., 1H)

MS: ES– 364

Example 15 2-(4-Chlorophenyl)-2-(1-((1,3,5-trimethyl-1H-pyrazol-4-yl)sulfonyl)piperidin-4-ylidene)acetonitrile

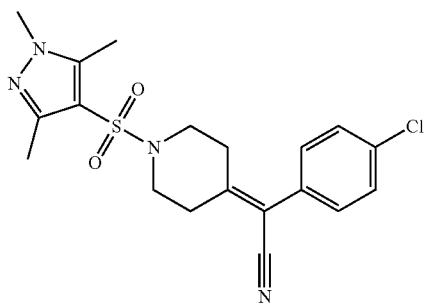 [SMILES: Cc1nn(C)c(C)c1S(=O)(=O)N1CCC(=C(C#N)c2ccc(Cl)cc2)CC1]

Prepared as described for 2-(4-chlorophenyl)-2-(1-((3,5-dimethyl-1H-pyrazol-4-yl)sulfonyl)piperidin-4-ylidene)acetonitrile (Example 3) using 1,3,5-trimethyl-1H-pyrazole-4-sulfonyl chloride.

¹H NMR (400 MHz, DMSO-d₆) δ ppm 2.08-2.20 (m, 4H) 2.48-2.50 (m, 4H) 2.78 (s, 3H) 3.70 (s, 3H) 7.32-7.38 (m, 2H) 7.48-7.52 (m, 2H)

MS: ES+ 405

Example 16 4-((4-Chlorophenyl)fluoromethylene)-1-((3,5-dimethyl-1H-pyrazol-4-yl)sulfonyl)piperidine

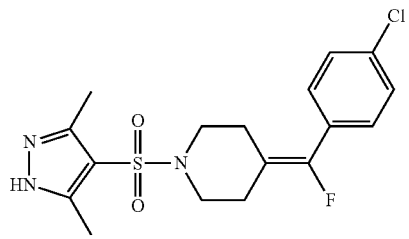 [SMILES: Cc1n[nH]c(C)c1S(=O)(=O)N1CCC(=C(F)c2ccc(Cl)cc2)CC1]

Prepared as described for methyl 2-(4-chlorophenyl)-2-(1-((3,5-dimethyl-1H-pyrazol-4-yl)sulfonyl)piperidin-4-ylidene)acetate (Example 2) from 3,5-dimethyl-1H-pyrazole-4-sulfonyl chloride (Intermediate 1, 232 mg, 1.194 mmol) and 4-((4-chlorophenyl)fluoromethylene)piperidine hydrochloride (Intermediate 14, 313 mg, 1.194 mmol) to afford the title compound (0.31 g, 67%).

¹H NMR (400 MHz, DMSO-d₆) δ ppm 2.25-2.42 (m, 10H) 2.96-3.08 (m, 4H) 7.40-7.46 (m, 2H) 7.48-7.52 (m, 2H) 13.0 (s, 1H)

MS: ES+ 384

Example 17 4-((3-Chloro-4-fluorophenyl)fluoromethylene)-1-((3,5-dimethyl-1H-pyrazol-4-yl)sulfonyl)piperidine

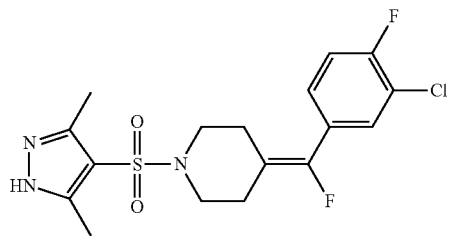 [SMILES: Cc1n[nH]c(C)c1S(=O)(=O)N1CCC(=C(F)c2ccc(F)c(Cl)c2)CC1]

Prepared as described for methyl 2-(4-chlorophenyl)-2-(1-((3,5-dimethyl-1H-pyrazol-4-yl)sulfonyl)piperidin-4-ylidene)acetate (Example 2) from 3,5-dimethyl-1H-pyrazole-4-sulfonyl chloride (Intermediate 1, 217 mg, 1.11 mmol) and 4-((3-chloro-4-fluorophenyl)fluoromethylene)piperidine hydrochloride (Intermediate 15, 312 mg, 1.11 mmol) to afford the title compound (0.19 g, 42%).

¹H NMR (400 MHz, DMSO-d₆) δ ppm 2.20-2.35 (m, 10H) 2.86-3.10 (m, 4H) 7.40-7.50 (m, 2H) 7.64-7.70 (m, 1H) 13.0 (s, 1H)

MS: ES+ 402

Example 18 4-((2,4-Dichlorophenyl)fluoromethylene)-1-((3,5-dimethyl-1H-pyrazol-4-yl)sulfonyl)piperidine

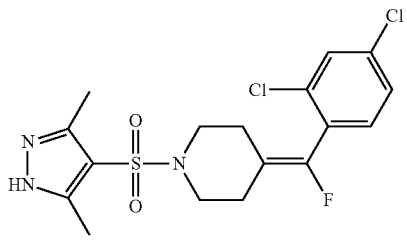 [SMILES: Cc1n[nH]c(C)c1S(=O)(=O)N1CCC(=C(F)c2ccc(Cl)cc2Cl)CC1]

Prepared as described for methyl 2-(4-chlorophenyl)-2-(1-((3,5-dimethyl-1H-pyrazol-4-yl)sulfonyl)piperidin-4-ylidene)acetate (Example 2) from 3,5-dimethyl-1H-pyrazole-4-sulfonyl chloride (Intermediate 1, 260 mg, 1.33 mmol) and 4-((2,4-dichlorophenyl)fluoromethylene)piperidine hydrochloride (Intermediate 16, 480 mg, 1.33 mmol) to afford the title compound (0.26 g, 48%).

¹H NMR (400 MHz, DMSO-d₆) δ ppm 2.00-2.15 (m, 2H) 2.20-2.40 (br s, 6H) 2.50-2.55 (m, 2H) 2.85-2.96 (m, 2H) 3.08-3.12 (m, 2H) 7.40-7.44 (m, 2H) 7.55 (s, 1H) 13.0 (s, 1H)

MS: ES+ 418

Example 19 4-((3,4-Dichlorophenyl)fluoromethylene)-1-((3,5-dimethyl-1H-pyrazol-4-yl)sulfonyl)piperidine

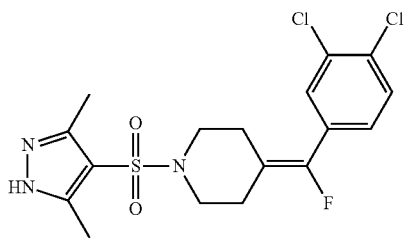 [SMILES: Cc1n[nH]c(C)c1S(=O)(=O)N1CCC(=C(F)c2ccc(Cl)c(Cl)c2)CC1]

Prepared as described for methyl 2-(4-chlorophenyl)-2-(1-((3,5-dimethyl-1H-pyrazol-4-yl)sulfonyl)piperidin-4-ylidene)acetate (Example 2) from 3,5-dimethyl-1H-pyrazole-4-sulfonyl chloride (Intermediate 1, 385 mg, 1.97 mmol) and 4-((3,4-dichlorophenyl)fluoromethylene)piperidine hydrochloride (Intermediate 17; 712 mg, 1.97 mmol) to afford the title compound (0.57 g, 69%).

¹H NMR (400 MHz, DMSO-d₆) δ ppm 2.20-2.40 (m, 10H) 2.90-3.10 (m, 4H) 7.39-7.45 (m, 1H) 7.70-7.80 (m, 2H) 13.0 (s, 1H)

MS: ES+ 418

Example 20 4-((4-Chloro-3-fluorophenyl)fluoromethylene)-1-((3,5-dimethyl-1H-pyrazol-4-yl)sulfonyl)piperidine

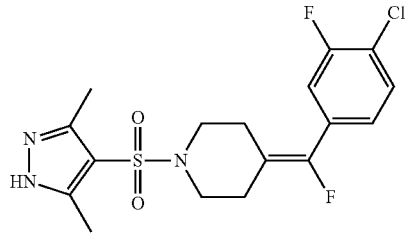 [SMILES: Cc1n[nH]c(C)c1S(=O)(=O)N1CCC(=C(F)c2ccc(Cl)c(F)c2)CC1]

Prepared as described for methyl 2-(4-chlorophenyl)-2-(1-((3,5-dimethyl-1H-pyrazol-4-yl)sulfonyl)piperidin-4-ylidene)acetate (Example 2) from 3,5-dimethyl-1H-pyrazole-4-sulfonyl chloride (Intermediate 1, 178 mg, 0.91 mmol) and 4-((4-chloro-3-fluorophenyl)fluoromethylene)piperidine hydrochloride (Intermediate 18, 256 mg, 0.91 mmol) to afford the title compound (0.23 g, 61%).

$^1$H NMR (400 MHz, DMSO-$d_6$) δ ppm 2.20-2.50 (m, 10H) 2.95-3.12 (m, 4H) 7.25-7.31 (m, 1H) 7.42-7.48 (m, 1H) 7.58-7.67 (m, 1H) 13.0 (s, 1H)

MS: ES+ 402

Example 21 4-((4-Chloro-2-fluorophenyl)fluoromethylene)-1-((3,5-dimethyl-1H-pyrazol-4-yl)sulfonyl)piperidine

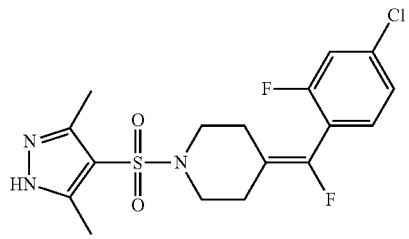 [SMILES: Cc1n[nH]c(C)c1S(=O)(=O)N1CCC(=C(F)c2ccc(Cl)cc2F)CC1]

Prepared as described for methyl 2-(4-chlorophenyl)-2-(1-((3,5-dimethyl-1H-pyrazol-4-yl)sulfonyl)piperidin-4-ylidene)acetate (Example 2) from 3,5-dimethyl-1H-pyrazole-4-sulfonyl chloride (Intermediate 1, 25 mg, 0.13 mmol) and 4-((4-chloro-2-fluorophenyl)fluoromethylene)piperidine hydrochloride (Intermediate 19, 45 mg, 0.13 mmol) to afford the title compound (0.036 g, 68%).

$^1$H NMR (400 MHz, DMSO-$d_6$) δ ppm 2.14-2.18 (m, 2H) 2.26 (s, 3H) 2.36 (s, 3H) 2.48-2.53 (m, 2H) 2.96-3.08 (m, 2H) 3.10-3.16 (m, 2H) 7.36-7.41 (m, 1H) 7.47-7.52 (m, 1H) 7.58-7.67 (m, 1H) 13.0 (s, 1H)

MS: ES+ 402

Example 22 4-((2,4-Difluorophenyl)fluoromethylene)-1-((3,5-dimethyl-1H-pyrazol-4-yl)sulfonyl)piperidine

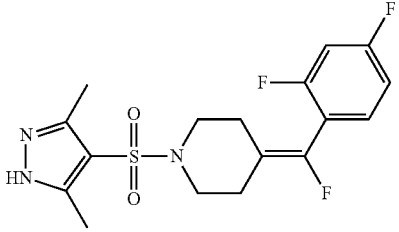 [SMILES: Cc1n[nH]c(C)c1S(=O)(=O)N1CCC(=C(F)c2ccc(F)cc2F)CC1]

Prepared as described for methyl 2-(4-chlorophenyl)-2-(1-((3,5-dimethyl-1H-pyrazol-4-yl)sulfonyl)piperidin-4-ylidene)acetate (Example 2) from 3,5-dimethyl-1H-pyrazole-4-sulfonyl chloride (Intermediate 1, 892 mg, 4.58 mmol) and 4-((2,4-difluorophenyl)fluoromethylene)piperidine hydrochloride (Intermediate 20, 1039 mg, 4.58 mmol) to afford the title compound (1.2 g, 68%).

$^1$H NMR (400 MHz, DMSO-$d_6$) δ ppm 2.16-2.22 (m, 2H) 2.34-2.45 (m, 6H) 2.55-2.60 (m, 2H) 2.91-3.08 (m, 2H) 3.10-3.22 (m, 2H) 7.14-7.22 (m, 1H) 7.31-7.38 (m, 1H) 7.38-7.55 n (m, 1H) 13.0 (s, 1H)

MS: ES+ 400

Example 23 3-((1-((3,5-Dimethyl-1H-pyrazol-4-yl)sulfonyl)piperidin-4-ylidene) fluoromethyl) quinoline

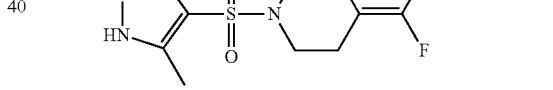

Prepared as described for methyl 2-(4-chlorophenyl)-2-(1-((3,5-dimethyl-1H-pyrazol-4-yl)sulfonyl)piperidin-4-ylidene)acetate (Example 2) from 3,5-dimethyl-1H-pyrazole-4-sulfonyl chloride (Intermediate 1, 117 mg, 0.59 mmol) and 3-(fluoro(piperidin-4-ylidene)methyl)quinoline hydrochloride (Intermediate 21, 167 mg, 0.59 mmol) to afford the title compound (0.045 g, 18%).

$^1$H NMR (400 MHz, DMSO-$d_6$) δ ppm 2.25-2.41 (m, 6H) 2.45-3.50 (m, 2H) 2.62-2.65 (m, 2H) 2.99-3.05 (m, 2H) 3.08-3.12 (m, 2H) 7.67-7.71 (m, 1H) 7.80-7.90 (m, 1H) 8.05-8.10 (m, 2H) 8.45 (s, 1H) 8.90 (s, 1H) 13.0 (s, 1H)

MS: ES+ 401

3. BIOLOGICAL ASSAY

Prokineticin receptor 1 (PKR1) antagonists may be functionally assessed by measurement of change in intracellular calcium levels induced by Gq mediated increase in inositol triphosphate (IP3) levels. The ability of a compound to block the intracellular release of calcium mediated by PK1 in RBL2H3 cells expressing human PKR1 receptors is determined as a measure of the compound's antagonist activity in vitro.

Approximately 10,000 cells per assay well are seeded in normal culture medium in a 384 well plate (Corning). Twenty-four hours after seeding, the cells are loaded with a calcium sensitive fluorescent dye by replacing the culture medium with assay buffer (1× Hanks buffered saline, 25 mM HEPES, 0.1% w/v fatty acid free BSA (bovine serum albumin), pH 7.4) containing 1 mM probenecid and 1× Calcium 5 Reagent (Molecular Devices). Cells are incubated at 37° C. for 1 hour to allow for dye uptake.

To test for antagonist activity, test compounds at a final concentration range between 0.32 nM-10 μM (diluted in assay buffer) are added to the assay wells and allowed to incubate for 10 minutes prior to stimulation with PK1. After incubation with test compounds the assay plate is placed in a FLIPR Tetra (Molecular Devices) and PK1 (diluted in assay buffer) is added at the determined EC80 concentration (final). Ligand-dependent changes in intracellular calcium levels are determined by measuring changes in fluorescence of the dye at 525 nM following excitation at 485 nM. Readings from wells that do not contain antagonist enable percentage inhibition curves to be plotted using 4-parameter fit algorithm and $IC_{50}$ values are calculated for each test compound.

Results

| Compound of Example No. | Mean $IC_{50}$ (μM) | Compound of Example No. | Mean $IC_{50}$ (μM) |
|---|---|---|---|
| 1 | 1.37 | 2 | 3.10 |
| 3 | 0.04 | 4 | 3.68 |
| 5 | 0.18 | 6 | 0.05 |
| 7 | 0.21 | 8 | 5.43 |
| 9 | 0.15 | 10 | 0.47 |
| 11 | 0.60 | 12 | 0.55 |
| 13 | 0.76 | 14 | 0.76 |
| 15 | 0.04 | 16 | 0.16 |
| 17 | 1.88 | 18 | 0.26 |
| 19 | 0.52 | 20 | 0.19 |
| 21 | 0.40 | 22 | 1.63 |
| 23 | 0.06 | | |

The compounds tested above exhibit $IC_{50}$ values significantly less than 10 μM, with the most potent compounds showing antagonist activity at the prokineticin receptor with $IC_{50}$ values <1 μM.

The invention claimed is:

1. A method of treating irritable bowel syndrome or inflammatory bowel disease comprising administering to a patient in need thereof a compound selected from:
   Methyl 2-(4-Chlorophenyl)-2-(1-((3,5-dimethyl-1H-pyrazol-4-yl)sulfonyl)piperidin-4-ylidene)acetate,
   2-(4-Chlorophenyl)-2-(1-((3,5-dimethyl-1H-pyrazol-4-yl)sulfonyl)piperidin-4-ylidene)acetonitrile,
   2-(2,6-Difluorophenyl)-2-(1-((3,5-dimethyl-1H-pyrazol-4-yl)sulfonyl)piperidin-4-ylidene)acetonitrile,
   2-(4-Chloro-2-fluorophenyl)-2-(1-((3,5-dimethyl-1H-pyrazol-4-yl)sulfonyl)piperidin-4-ylidene)acetonitrile,
   2-(4-Chlorophenyl)-2-(1-((3,5-diethyl-1H-pyrazol-4-yl)sulfonyl)piperidin-4-ylidene)acetonitrile,
   2-(4-Chlorophenyl)-2-(1-((1,5-dimethyl-3-(trifluoromethyl)-1H-pyrazol-4-yl)sulfonyl)piperidin-4-ylidene)acetonitrile,
   2-(2,6-Difluorophenyl)-2-(1-((1,3,5-trimethyl-1H-pyrazol-4-yl)sulfonyl)piperidin-4-ylidene)acetonitrile,
   2-(1-((3,5-Dimethyl-1H-pyrazol-4-yl)sulfonyl)piperidin-4-ylidene)-2-(4-(trifluoromethoxy)phenyl)acetonitrile,
   2-(4-Chlorophenyl)-2-(1-((3,5-dimethyl-1H-pyrazol-4-yl)sulfonyl)-3-methylpiperidin-4-ylidene)acetonitrile,
   4-(4-Chloro-2-fluorobenzylidene)-1-((3,5-dimethyl-1H-pyrazol-4-yl)sulfonyl)piperidine,
   4-(4-Chloro-2-fluorobenzylidene)-1-((1,3,5-trimethyl-1H-pyrazol-4-yl)sulfonyl)piperidine,
   4-(1-(4-Chlorophenyl)ethylidene)-1-((3,5-dimethyl-1H-pyrazol-4-yl)sulfonyl)piperidine,
   4-(4-Chlorobenzylidene)-1-((3,5-dimethyl-1H-pyrazol-4-yl)sulfonyl)piperidine,
   2-(4-Chlorophenyl)-2-(1-((1,3,5-trimethyl-1H-pyrazol-4-yl)sulfonyl)piperidin-4-ylidene)acetonitrile,
   4-((4-Chlorophenyl)fluoromethylene)-1-((3,5-dimethyl-1H-pyrazol-4-yl)sulfonyl)piperidine,
   4-((3-Chloro-4-fluorophenyl)fluoromethylene)-1-((3,5-dimethyl-1H-pyrazol-4-yl)sulfonyl)piperidine,
   4-((2,4-Dichlorophenyl)fluoromethylene)-1-((3,5-dimethyl-1H-pyrazol-4-yl)sulfonyl)piperidine,
   4-((3,4-Dichlorophenyl)fluoromethylene)-1-((3,5-dimethyl-1H-pyrazol-4-yl)sulfonyl)piperidine,
   4-((4-Chloro-3-fluorophenyl)fluoromethylene)-1-((3,5-dimethyl-1H-pyrazol-4-yl)sulfonyl)piperidine,
   4-((4-Chloro-2-fluorophenyl)fluoromethylene)-1-((3,5-dimethyl-1H-pyrazol-4-yl)sulfonyl)piperidine,
   4-((2,4-Difluorophenyl)fluoromethylene)-1-((3,5-dimethyl-1H-pyrazol-4-yl)sulfonyl)piperidine,
   3-((1-((3,5-Dimethyl-1H-pyrazol-4-yl)sulfonyl)piperidin-4-ylidene)fluoromethyl)quinoline, and pharmaceutically acceptable salts of any one thereof.

2. The method of treating irritable bowel syndrome or inflammatory bowel disease according to claim 1, further comprising administering to the patient in need thereof at least one additional therapeutic agent.

3. The method of treating irritable bowel syndrome or inflammatory bowel disease according to claim 1, wherein the compound is 4-((4-chloro-3-fluorophenyl)fluoromethylene)-1-((3,5-dimethyl-1H-pyrazol-4-yl)sulfonyl)piperidine or a pharmaceutically acceptable salt thereof.

4. The method of treating irritable bowel syndrome or inflammatory bowel disease according to claim 1, wherein the compound is 4-((4-chloro-2-fluorophenyl)fluoromethylene)-1-((3,5-dimethyl-1H-pyrazol-4-yl)sulfonyl)piperidine or a pharmaceutically acceptable salt thereof.

5. The method of treating irritable bowel syndrome or inflammatory bowel disease according to claim 3, further comprising administering to the patient in need thereof at least one additional therapeutic agent.

6. The method of treating irritable bowel syndrome or inflammatory bowel disease according to claim 4, further comprising administering to the patient in need thereof at least one additional therapeutic agent.

* * * * *